United States Patent
Khosravifar et al.

(10) Patent No.: US 10,604,809 B2
(45) Date of Patent: Mar. 31, 2020

(54) METHODS AND KITS FOR THE DIAGNOSIS AND TREATMENT OF PANCREATIC CANCER

(71) Applicant: Beth Israel Deaconess Medical Center, Inc., Boston, MA (US)

(72) Inventors: Roya Khosravifar, Jamaica Plain, MA (US); Towia Aron Libermann, Chestnut Hill, MA (US); Manoj K. Bhasin, Acton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 261 days.

(21) Appl. No.: 15/116,272

(22) PCT Filed: Feb. 4, 2015

(86) PCT No.: PCT/US2015/014490
§ 371 (c)(1),
(2) Date: Aug. 3, 2016

(87) PCT Pub. No.: WO2015/120069
PCT Pub. Date: Aug. 13, 2015

(65) Prior Publication Data
US 2016/0348182 A1    Dec. 1, 2016

Related U.S. Application Data

(60) Provisional application No. 61/935,711, filed on Feb. 4, 2014.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| 2003/0166629 | A1 | 9/2003 | Choi et al. |
| 2005/0009067 | A1* | 1/2005 | Logsdon ............ G01N 33/507 435/6.16 |

OTHER PUBLICATIONS

Grutzmann (Neoplasia vol. 6 No. 5 Sep./Oct. 2004 pp. 611-622).*
Chan (G&P magazine 2006 vol. 6 No. 3 pp. 20-26).*
Whitehead (Genome Biology 2005 vol. 6 Issue 2 Article R13).*
Coleman (Drug Discovery Today. 2003. 8: 233-235).*
Badea (Hapato-Gastroenterology 2008 vol. 55 pp. 2015-2026).*
Kulkarni (Current Protocols in Molecular Biology 25B.10.0-25B.10.17, Apr. 2011).*
Ohuchida (Clin Cancer Res 2006;12(7) Apr. 1, 2006).*
International Preliminary Report on Patentability for International Application No. PCT/US2015/014490, dated Aug. 9, 2016 (9 pages).
International Search Report and Written Opinion for International Application No. PCT/US15/14490, dated Apr. 23, 2015 (16 pages).
Samuel et al., "Integrated genomic, transcriptomic, and RNA-interference analysis of genes in somatic copy number gains in pancreatic ductal adenocarcinoma," Pancreas. 42(6):1016-26 (2013).
Badea et al., "Combined gene expression analysis of whole-tissue and microdissected pancreatic ductal adenocarcinoma identifies genes specifically overexpressed in tumor epithelia," Hepategastroenterology. 55(88):2015-26 (2008).

* cited by examiner

*Primary Examiner* — Amanda Haney
(74) *Attorney, Agent, or Firm* — Clark & Elbing LLP

(57) ABSTRACT

The present disclosure relates to the identification of genes and gene combinations that are correlated with patients having or being predisposed to developing pancreatic ductal adenocarcinoma (PDAC). In some instances, methods herein utilize panels of 5 or 10 genes to accurately diagnose PDAC, determine the likelihood of developing PDAC, or determine the severity/stages of PDAC. These panels may be used in a molecular diagnostic test.

17 Claims, 19 Drawing Sheets

Twenty-four hours after the sh100P infection, Capanc-1 (A) and BxPC3 (B) cells were seeded into soft agar at a density of 10000 cells/ well and allowed to grow for 21 day. Twenty-four hours after the shTMPRSS4 infection, BcPC3 (C) and Capanc-1 (D) cells were seeded into soft agar at a density of 10000 cells/well in six well plates, and allowed to grow for 21 days.

METHODS AND KITS FOR THE DIAGNOSIS AND TREATMENT OF PANCREATIC CANCER

BACKGROUND OF THE INVENTION

Pancreatic ductal adenocarcinoma (PDAC), the fourth leading cause of cancer death in the United States, is a devastating disease marked by an exceptionally high mortality rate nearly equivalent to its incidence. The median survival for a patient diagnosed with PDAC ranges from 4.5 months for the most advanced stage of the disease to 24.1 months for the earliest stage (Bilimoria et al. Cancer 2007; 110:738). Surgery is currently the treatment that provides the best chance of prolonged survival (five year survival of 20-25% vs <6% overall), however surgery is generally performed only at the earliest stages (American Cancer Society, Cancer Facts & Figures 2013). In the US, only about 15-20% of pancreatic cancer cases are diagnosed early enough to be eligible for surgery. Even if a pancreatic abnormality is identified before the onset of symptoms, there are no validated biomarkers that distinguish benign pancreatic lesions from pre-cancerous tumors or early-stage pancreatic cancer. Rather, current clinical diagnosis is based on a pathologist's visual inspection of tissue samples. A proven biomarker panel could dramatically improve PDAC screening in at-risk populations.

PDAC diagnosis is further complicated by limitations of imaging and histopathology and, in some cases, the difficulty of distinguishing PDAC from non-malignant pancreatic diseases. Recent advances in endoscopic ultrasound (EUS) have yielded improved sensitivity for PDAC identification. Nevertheless, differentiating between PDAC and benign disease remains difficult and can require multiple biopsies during multiple procedures. Even after two EUS fine needle aspiration (FNA) biopsy procedures, the diagnosis remains unknown for 7% of all patients with a pancreatic abnormality. This results in diagnostic uncertainty and delays in potentially curative treatment. Thus, a key unmet medical need with immediate clinical utility is an effective diagnostic test that accurately differentiates between PDAC and non-malignant pancreatic disorders such as chronic pancreatitis.

The rapid improvement in imaging quality and the number of imaging procedures (26 million annually in the US) has led to a rise in the identification of potential PDAC precursor lesions such as intraductal papillary mucinous neoplasms (IPMNs) and mucinous cystic neoplasms (MCNs). Although resection of precursor lesions prior to progression to invasive cancer is associated with better survival, accurate differential diagnosis of which lesions will progress to invasive cancer or harbor already malignant cells is necessary as the morbidity and mortality of surgery can be high. Unfortunately, with current diagnostic techniques the malignant potential of precursor lesions is often uncertain. Therefore, there is an unmet need for methods for the accurate determination of the likelihood of precursor legions developing into PDAC.

SUMMARY OF THE INVENTION

The present disclosure relates to the identification of genes and gene combinations that are correlated with patients having or being predisposed to developing PDAC. In some instances, methods herein utilize panels of 5 or 10 genes to accurately diagnose PDAC, determine the likelihood of developing PDAC, or determine the severity/stages of PDAC. These panels may be used in a molecular diagnostic test. On one hand, the methods herein will be a novel quantitative companion to the current subjective IHC clinical diagnostics for patients who undergo FNA biopsies. On the other hand, this strategy will also provide a non-invasive test enabling routine screening of at-risk patients who hold a genetic disposition, have a pancreatic disease, or are in an advanced age group as well as any patient with incidental findings of pancreatic cysts.

Accordingly, in a first aspect, the invention features a method for diagnosing PDAC, determining the likelihood of developing PDAC, or determining the severity of PDAC in a subject. This method includes determining an expression level of a panel of at least two (e.g., two three, four, five, six, seven, eight, nine, ten, twelve, fifteen, twenty, twenty-five, thirty, or more) genes (e.g., including gene products, as described herein) in a biological sample obtained from the subject, wherein an increased, decreased level or change in ratio (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase by more than about 10%, about 15%, about 20%, about 50%, about 75%, about 100%, or about 200%; a decrease by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more) for the panel of at least two genes in the biological sample, as compared to a control (e.g., a control sample from a subject that does not have PDAC), is indicative of the presence of PDAC, an increased likelihood of developing PDAC, an increased severity of PDAC, or is indicative of predicting outcome, disease-free survival, overall survival, response to therapy, resistance or recurrence of the disease and wherein the panel of at least two genes comprises at least two of: epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); and CUB and zona pellucid-like domains 1 (CUZD1).

In another aspect, the invention features a method for diagnosing PDAC, determining the likelihood of developing PDAC, or determining the severity of PDAC in a subject, or predicting outcome, disease-free survival, overall survival, response to therapy, resistance or recurrence of the disease, or monitoring response to therapy. This method includes: (a) contacting a biological sample obtained from the subject with one or more (e.g., more than one, more than two, more than three, more than five, more than six, more than seven, more than eight, more than nine, more than ten, more than twelve, more than fifteen, more than twenty, more than twenty-five, or more than thirty) binding agents capable of specifically binding one or more genes (e.g., more than one, more than two, more than three, more than five, more than six, more than seven, more than eight, more than nine, more than ten, more than twelve, more than fifteen, more than twenty, more than twenty-five, or more than thirty) or a protein encoded by said one or more (e.g., more than two, more than three, more than five, more than six, more than seven, more than eight, more than nine, more than ten, more than twelve, more than fifteen, more than twenty, more than twenty-five, or more than thirty) genes; and (b) determining the expression level of a panel of at least two genes in the biological sample, wherein an increased or decreased level (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase by more than about 10%, about 15%, about 20%, about 50%, about 75%, about 100%, or about 200%; a decrease by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more) for the panel of at least two (e.g., three, four, five, six, seven, eight, nine, ten, twelve, fifteen, twenty, twenty-five, thirty, or more) genes in the biological sample, as compared to a control is indicative of the presence of PDAC, an increased likelihood of developing PDAC, or increased severity of PDAC, or is indicative of predicting outcome, disease-free survival, overall survival, response to therapy, resistance or recurrence of the disease and wherein the panel of at least two genes comprises at least two of: epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); and CUB and zona pellucid-like domains 1 (CUZD1).

In another aspect, the invention features a method for treatment of pancreatic ductal adenocarcinoma in a subject, the method includes: (a) contacting a biological sample obtained from the subject with one or more binding agents capable of specifically binding one or more genes or a protein encoded by the one or more genes; (b) determining if the expression level of a panel of at least two genes in the biological sample is changed relative to a control sample, wherein the panel of at least two genes comprises at least two of: epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); and CUB and zona pellucid-like domains 1 (CUZD1); (c) predicting a response to a pancreatic ductal adenocarcinoma therapy in the subject based on the level of expression or activation of one or more of the genes; (d) administering a pancreatic ductal adenocarcinoma therapy to the subject based on a prediction of a positive response to said therapy.

In another aspect, the invention features a method for treatment of pancreatic ductal adenocarcinoma in a subject, the method includes: (a) determining if the expression level of a panel of at least two genes in a biological sample obtained from the subject is changed relative to a control sample, wherein the panel of at least two genes comprises at least two of: epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); and CUB and zona pellucid-like domains 1 (CUZD1); (b) predicting a response to a pancreatic ductal adenocarcinoma therapy in the subject based on the level of expression of one or more of the biomarkers; (c) administering a pancreatic ductal adenocarcinoma therapy to the subject based on a prediction of a positive response to the therapy.

In some embodiments, an increased or decreased level of expression for one or more genes as compared to a control is indicative of a positive response to therapy in pancreatic ductal adenocarcinoma.

In certain embodiments, a pancreatic ductal adenocarcinoma therapy is administered to the patient upon a prediction of a positive response to said pancreatic ductal adenocarcinoma therapy based on increased gene expression of said one or more genes.

In other embodiments, the pancreatic ductal adenocarcinoma therapy includes administering a therapeutic agent that targets the gene, gene product, or regulatory RNAs of any one of epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); or CUB and zona pellucid-like domains 1 (CUZD1).

In certain embodiments, the pancreatic ductal adenocarcinoma therapy includes administering at least one therapeutic agent that targets at least two genes, gene products, or regulatory RNAs of epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); or CUB and zona pellucid-like domains 1 (CUZD1).

In some embodiments, the method further includes administering further includes administering an additional pancreatic ductal adenocaricnoma therapy (e.g., an antiproliferative agent such as, erlotinib, fluorouracil, gemcitabine, mitomycin C, or oxaliplatin).

In some embodiments of any of the foregoing methods, the method further includes performing an endoscopic ultrasound fine needle aspiration biopsy.

In some embodiments of any of the foregoing methods, the panel of at least two genes includes ECT2, AHNAK2, SERPINB5, TMPRSS4, POSTN, S100P, CEACAM5, GABRP, CELA2B, and CUZD1.

In some embodiments, the panel of at least two genes consists of ECT2, AHNAK2, SERPINB5, TMPRSS4, and POSTN.

In other embodiments, the panel of at least two genes consists of ECT2, AHNAK2, SERPINB5, TMPRSS4, POSTN, S100P, CEACAM5, GABRP, CELA2B, and CUZD1.

In another aspect, the invention features a kit or device for diagnosing a subject having, or having a predisposition to develop, pancreatic ductal adenocarcinoma and/or predicting response to pancreatic ductal adenocarcinoma therapy, said kit including:

(a) a set of two or more binding agents (e.g., two, more than two, more than three, more than five, more than six, more than seven, more than eight, more than nine, more than ten, more than twelve, more than fifteen, more than twenty, more than twenty-five, or more than thirty), each of said binding agents capable of specifically binding to at least one or more (e.g., more than one, more than two, more than three, more than five, more than six, more than seven, more than eight, more than nine, more than ten, more than twelve, more than fifteen, more than twenty, more than twenty-five, or more than thirty) genes or a protein encoded by said one or more (e.g., more than one, more than two, more than three, more than five, more than six, more than seven, more than eight, more than nine, more than ten, more than twelve, more than fifteen, more than twenty, more than twenty-five, or more than thirty) genes selected from the group consisting of: epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); and CUB and zona pellucid-like domains 1 (CUZD1); and (b) instructions for use of said kit to determine the expression level of said genes or said protein encoded by said genes;

wherein an increased expression level of epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); and/or gamma-aminobutyric acid (GABA) A receptor, pi (GABRP), as compared to a reference sample, is indicative that said subject has or has a predisposition to develop, pancreatic ductal adenocarcinoma and/or a positive response to pancreatic ductal adenocarcinoma therapy; and/or wherein a decreased expression level of chymotrypsin-like elastase family, member 2B (CELA2B); and/or CUB and zona pellucid-like domains 1 (CUZD1)), as compared to a reference sample, is indicative that said subject has or has a predisposition to develop, pancreatic ductal adenocarcinoma and/or a positive response to pancreatic ductal adenocarcinoma therapy.

In some embodiments of the kit or device, the set of two or more binding agents includes binding agents capable of specifically binding to ECT2, AHNAK2, SERPINB5, TMPRSS4, and POSTN.

In some embodiments of the kit or device, the set of two or more binding agents consists of binding agents capable of specifically binding to ECT2, AHNAK2, SERPINB5, TMPRSS4, and POSTN.

In some embodiments of the kit or device, the set of two or more binding agents includes binding agents capable of specifically binding to ECT2, AHNAK2, SERPINB5, TMPRSS4, POSTN, S100P, CEACAM5, GABRP, CELA2B, and CUZD1.

In other embodiments of the kit or device, the set of two or more binding agents consists of binding agents capable of specifically binding to ECT2, AHNAK2, SERPINB5, TMPRSS4, POSTN, S100P, CEACAM5, GABRP, CELA2B, and CUZD1.

In some embodiments of the kit or device, the one or more binding agents are polynucleotides, small molecules or polypeptides, such as antibodies (e.g., provided on solid support e.g., a well, a plate, a wellplate, a tube, an array, a bead, a disc, a microarray, or a microplate, e.g., a microarray).

In another aspect, the invention features a method for diagnosing pancreatic ductal adenocarcinoma, determining the likelihood of developing pancreatic ductal adenocarcinoma, a precursor of pancreatic ductal adenocarcinoma, or an increased severity of pancreatic ductal adenocarcinoma, predicting a response to therapy, or determining the severity of pancreatic ductal adenocarcinoma in a subject, the method includes determining the expression level of a panel of at least two genes in a biological sample obtained from said subject with any of the foregoing kits or devices.

In another aspect, the invention features a method for treatment of pancreatic ductal adenocarcinoma in a subject, the method includes:

(a) determining the expression level of a panel of at least two genes in the biological sample with any of the foregoing kits or devices;

(b) predicting a response to a pancreatic ductal adenocarcinoma therapy in the subject based on the level of expression of one or more of the genes; and (c) administering a pancreatic ductal adenocarcinoma therapy to the subject based on a prediction of a positive response to said therapy.

In some embodiments, the pancreatic ductal adenocarcinoma therapy includes administering a therapeutic agent that targets the gene, gene product, or regulatory RNAs of any one of epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); or CUB and zona pellucid-like domains 1 (CUZD1).

In other embodiments, the said pancreatic ductal adenocarcinoma therapy includes administering at least one therapeutic agent that targets at least two genes, gene products, or RNA regulatory of epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); or CUB and zona pellucid-like domains 1 (CUZD1).

In certain embodiments, the method further includes administering an additional pancreatic ductal adenocaricnoma therapy (e.g., an antiproliferative such as, erlotinib, fluorouracil, gemcitabine, mitomycin C, or oxaliplatin).

In some embodiments, the method further includes performing an endoscopic ultrasound fine needle aspiration biopsy.

In certain embodiments of any of the foregoing methods, the expression level is mRNA expression level, cDNA expression level, or protein expression level.

In further embodiments of any of the foregoing methods, the biological sample includes mRNA, cDNA, and/or protein from the subject.

In some embodiments of any of the foregoing methods, the expression level is determined by one or more of a hybridization assay, an amplification-based assay, a single molecule detection assay, a sequencing assay, or fluorescence in situ hybridization assay.

In other embodiments, the method further includes directly analyzing RNA without extraction and without conversion into cDNA.

In other embodiments, the method further includes prior to determining the expression level, extracting mRNA from the biological sample and reverse transcribing the mRNA into cDNA to obtain a treated biological sample.

In still further embodiments of any of the foregoing methods, the method further includes contacting the biological sample with one or more binding agents capable of specifically binding one or more of the panel of at least two genes or a protein encoded by one or more of the panel of at least two genes.

In some embodiments of any of the foregoing methods, the subject is predisposed to developing PDAC (e.g., the subject has a family history of pancreatic cancer, is over the age of 60, has a history of smoking, is obese, has been diagnosed with diabetes mellitus, or has been diagnosed with chronic pancreatitis or has genetic predispositions such as mutations in BRCA1, BRCA2, ADAMST1, BCN1, PALB2, PRSS1, CDKN2A, or other predisposition genes).

In further embodiments of any of the foregoing methods, the subject is undergoing treatment for PDAC, and the level of expression of the panel of at least two genes is indicative of the efficacy of treatment.

In other embodiments of any of the foregoing methods, the biological sample is a tissue sample, whole blood, plasma, serum sample, urine, saliva, bile, or pancreatic juice.

In any of the aspects and embodiments described herein, the expression level is increased (e.g., an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, about 1000%, or more; or an increase by more than about 10%, about 15%, about 20%, about 50%, about 75%, about 100%, about 200%, about 300%, about 400%, about 500%, about 1000%, or more, as compared to a control). In some embodiments, the expression level is increased (e.g., by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more, as compared to a control). In any of the aspects and embodiments described herein, the expression level is decreased (e.g., a decrease by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, about 300%, about 400%, about 500%, about 1000%, or more; or a decrease by more than about 10%, about 15%, about 20%, about 50%, about 75%, about 100%, about 200%, about 300%, about 400%, about 500%, about 1000%, or more, as compared to a control). In some embodiments, the expression level is decreased (e.g., by less than about 0.01-fold, about 0.02-fold, about 0.1-fold, about 0.3-fold, about 0.5-fold, about 0.8-fold, or less, as compared to a control).

In any of the aspects and embodiments described herein, the sample obtained from the patient is selected from tissue, whole blood, blood-derived cells (e.g., one or more of T cells or total peripheral blood mononuclear cells), plasma, serum, urine, saliva, bile, pancreatic juice, and combinations thereof In any of the aspects and embodiments described herein, the expression level is determined by one or more of a hybridization assay (e.g., northern analysis, ELISA, immunohistochemical analysis, microarray, chip, microfluidic chip, sequencing, or western blotting), mass spectrometry, an amplification-based assay (e.g., PCR, quantitative PCR, or real-time quantitative PCR), amplification-free assay (e.g. Nanostring), microdroplet based assay, nanopore based assay, bead based assays (e. g. Luminex, nanoparticles, Nanosphere), nuclease protection assay, or fluorescence in situ hybridization.

In any of the aspects and embodiments described herein, the panel of at least two genes are selected from the group comprising: epithelial cell transforming sequence 2 oncogene (ECT2, UniGene Hs. 518299, Ref. Seq. No. NP_001245244.1); AHNAK nucleoprotein 2 (AHNAK2, Unigene Hs. 441783, Ref. Seq. Nos. NP_612429.2 and NM_138420.2); serpin peptidase inhibitor, Glade B (ovalbumin) member 5 (SERPINB5, Unigene Hs. 55279, Ref. Seq. Nos. NP_002630.2 and NM_002639.4); transmembrane protease, serine 4 (TMPRSS4, Unigene Hs. 161985, Ref. Seq. No. NP_063947.1); periostin, osteoblast specific factor (POSTN, Unigene Hs. 136348, Ref. Seq. No. NP_006466.2); S100 calcium binding protein P (S100P, Unigene Hs. 2962, Ref. Seq. Nos. NP_005971.1 and NM_005980.2); carcinoembryonic antigen-related cell adhesion molecule 5 (CEACAM5, Unigene Hs. 709196, Ref. Seq. Nos. NP_004354.2 and NM_004363.2); gamma-aminobutyric acid (GABA) A receptor, pi (GABRP, Unigene Hs. 26225, Ref. Seq. Nos. NP_055026.1 and NM_014211.2); chymotrypsin-like elastase family, member 2B (CELA2B, Unigene Hs. 631871, Ref. Seq. Nos. NP_056933.2 and NM_015849.2); and CUB and zona pellucid-like domains 1 (CUZD1, Unigene Hs. 647182, Ref. Seq. No. NP_071317.2 and NM).

In any of the aspects and embodiments described herein, the methods, compositions, and diagnostic kits include three or more genes. In some embodiments, the methods, compositions, and diagnostic kits include four or more (e.g., five, six, seven, eight, nine, ten, eleven, twelve, thirteen, fourteen, fifteen, sixteen, seventeen, eighteen, nineteen, twenty, twenty-five, thirty, or more) genes.

In any of the aspects and embodiments described herein, the panel of at least two genes includes ECT2. In any of the aspects and embodiments described herein, the panel of at least two genes includes AHNAK2. In any of the aspects and embodiments described herein, the panel of at least two genes includes SERPINB5. In any of the aspects and embodiments described herein, the panel of at least two genes includes TMPRSS4. In any of the aspects and embodiments described herein, the panel of at least two genes includes POSTN. In any of the aspects and embodiments described herein, the panel of at least two genes includes ECT2, AHNAK2, SERPINB5, TMPRSS4, and POSTN. In any of the aspects and embodiments described herein, the panel of at least two genes includes S100P. In any of the aspects and embodiments described herein, the panel of at least two genes includes CEACAM5. In any of the aspects and embodiments described herein, the panel of at least two genes includes GABRP. In any of the aspects and embodiments described herein, the panel of at least two genes includes CELA2B. In any of the aspects and embodiments described herein, the panel of at least two genes includes CUZD1.

In any of the aspects and embodiments described herein, the panel of at least two genes does not include ECT2. In any of the aspects and embodiments described herein, the panel of at least two genes does not include AHNAK2. In any of the aspects and embodiments described herein, the panel of at least two genes does not include SERPINB5. In any of the aspects and embodiments described herein, the panel of at least two genes does not include TMPRSS4. In any of the aspects and embodiments described herein, the panel of at least two genes does not include POSTN. In any of the aspects and embodiments described herein, the panel of at least two genes does not include ECT2, AHNAK2, SERPINB5, TMPRSS4, and POSTN. In any of the aspects and embodiments described herein, the panel of at least two genes does not include S100P. In any of the aspects and embodiments described herein, the panel of at least two genes does not include CEACAM5. In any of the aspects and embodiments described herein, the panel of at least two genes does not include GABRP. In any of the aspects and embodiments described herein, the panel of at least two genes does not include CELA2B. In any of the aspects and embodiments described herein, the panel of at least two genes does not include CUZD1.

In some embodiments, the expression level of each gene (e.g., ECT2, AHNAK2, SERPINB5, TMPRSS4, POSTN, S100P, CEACAM5, or GABRP) is increased (e.g., independently, an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more, as compared to a control). In some embodiments, the expression level of each gene (e.g., CELA2B or CUZD1) is decreased (e.g., independently, a decrease by less than about 0.01-fold, about 0.02-fold, about 0.1-fold, about 0.3-fold, about 0.5-fold, about 0.8-fold, or less, as compared to a control).

In any of the aspects and embodiments described herein, the one or more genes include one or more housekeeping genes (e.g., GAPDH or CD3E) or a control (e.g., HGDC).

In any of the aspects and embodiments described herein, the one or more genes include or consist of any combination described herein.

Also provided herein are methods of treating a patient with PDAC and other related diseases. The diagnostic tests disclosed herein can be used to determine an optimal treatment plan for a subject or to determine the efficacy of a treatment plan for a subject. For example, the subject can be treated for a disease and the prognosis of the disease can be determined by the diagnostic test disclosed herein. In particular embodiments, a diagnostic test or method is used to predict the risk a patient will develop PDAC. A diagnostic test or method can include a screen for gene expression profiles by any useful detection method (e.g., unlabeled, fluorescence, radiation, or chemiluminescence). A diagnostic test can further include one or more binding agents (e.g., one or more of probes, primers, peptides, small molecules, aptamers, or antibodies) to detect the expression of these genes. In certain embodiments, the diagnostic test includes the use of one or more genes associated with PDAC in a diagnostic platform, which can be optionally automated.

Provided herein are general strategies to develop diagnostic tests, which can be used to predict or diagnose PDAC, based on the expression profile of any of the genes disclosed herein. These strategies can be used to develop tests that use one or more of these genes, any combination of one or more of these genes, or one or more of these genes in combination with any other genes found to be associated with PDAC.

Also provided herein are methods of distinguishing other related diseases (e.g., pancreatitis, pancreatic cysts) from PDAC. Accordingly, the invention also includes methods of diagnosing a disease related to PDAC (e.g., pancreatitis) by performing any of the methods or using any of the compositions or kits described herein.

Other features and advantages of the invention will be apparent from the following description and the claims.

Definitions

As used herein, the term "about" means ±10% of the recited value.

The term "array" or "microarray," as used herein refers to an ordered arrangement of hybridizable array elements, preferably polynucleotide (e.g., oligonucleotides) or polypeptide (e.g., antibodies) probes, on a substrate. The substrate can be a solid substrate, such as a glass slide, beads, or microfluidic chip, or a semi-solid substrate, such as nitrocellulose membrane. The nucleotide sequences can be DNA, RNA, or any permutations or combinations thereof.

By a "binding agent" is meant a polynucleotide sequence or polypeptide sequence capable of specifically binding a target sequence, or a fragment thereof. By "specifically binds" is meant polynucleotide sequence or polypeptide sequence that recognizes and binds a particular target sequence, or a fragment thereof, but that does not substantially recognize and bind other molecules or other target sequences, including fragments thereof, in a sample, for example, a biological sample. In one example, a polynucleotide that specifically binds to an ECT2 binds to the DNA, mRNA, cDNA, or protein of ECT2, or a fragment thereof, but does not bind to other genes, gene products, or fragments thereof. In another example, a polypeptide that specifically binds to an ECT2 binds to the DNA, mRNA, cDNA, or protein of ECT2, or a fragment thereof, but does not bind to other genes, gene products, or fragments thereof. In another example, specific binding is determined under various conditions of stringency (See, e.g., Wahl et al., *Methods Enzymol.* 152:399 (1987); Kimmel, *Methods Enzymol.* 152:507 (1987)). For example, high stringency salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide. High stringency temperature conditions will ordinarily include temperatures of at least about 30° C., 37° C., or 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In an alternative embodiment, hybridization will occur at 50° C. or 70° C. in 400 mM NaCl, 40 mM PIPES, and 1 mM EDTA, at pH 6.4, after hybridization for 12-16 hours, followed by washing. Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. Useful variations on these conditions will be readily apparent to those skilled in the art.

By "biological sample" or "sample" is meant a solid or a fluid sample. Biological samples may include cells; polynucleotide, protein, or membrane extracts of cells (e.g., pancreas cells); or blood or biological fluids including, e.g., pancreatic fluid, saliva, urine, bile). Examples of solid biological samples include samples taken from feces, the rectum, central nervous system, bone, breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, and the thymus. Examples of fluid biological samples include samples taken from the blood, serum, pancreatic fluid, CSF, semen, prostate fluid, seminal fluid, urine, saliva, sputum, mucus, bone marrow, lymph, and tears. Samples may be obtained by standard methods including, e.g., venous puncture and surgical biopsy. In certain embodiments, the biological sample is a blood or serum sample.

By a "control" is meant any useful reference used to diagnose PDAC. The control can be any sample, standard, standard curve, or level that is used for comparison purposes. The control can be a normal reference sample or a reference standard or level. A "reference sample" can be, for example, a prior sample taken from the same subject; a sample from a normal healthy subject, such as a normal cell or normal tissue; a sample (e.g., a cell or tissue) from a subject not having PDAC, a related disease, or a condition to be differentiated from PDAC, such as pancreatitis; a sample from a subject that is diagnosed with a propensity to develop PDAC or a related disease but does not yet show symptoms of the disorder; a sample from a subject with incidental findings of pancreatic cysts, a sample from a subject that has been treated for a disease associated with PDAC; or a sample of a purified gene (e.g., any described herein) at a known normal concentration. By "reference standard or level" is meant a value or number derived from a reference sample. A normal reference standard or level can be a value or number derived from a normal subject who does not have a disease associated with PDAC, a related disease, or a condition to be differentiated from PDAC, such as pancreatitis. In preferred embodiments, the reference sample, standard, or level is matched to the sample subject by at least one of the following criteria: age, weight, sex, disease stage, and overall health. A standard curve of levels of a purified gene, e.g., any described herein, within the normal reference range can also be used as a reference.

By "diagnosing" is meant identifying a molecular or pathological state, disease or condition, such as the identification of PDAC or to refer to identification of a subject having PDAC who may benefit from a particular treatment regimen.

By "expression" is meant the detection of a gene, polynucleotide, or polypeptide by methods known in the art. For example, DNA expression is often detected by sequencing, microarray, Southern blotting or polymerase chain reaction (PCR), and RNA expression is often detected by sequencing, northern blotting, RT-PCR, gene array technology, or RNAse protection assays. Methods to measure protein expression level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of the protein including, but not limited to, enzymatic activity or interaction with other protein partners.

By "expression profile" is meant one or more expression values determined for a sample.

By "expression level of a gene" is meant a level of a gene or a gene product, such as mRNA, cDNA, or protein, as compared to a control. The control can be any useful reference, as defined herein. By a "decreased level" or an "increased level" of a gene is meant a decrease or increase in gene expression, as compared to a control (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase by more than about 10%, about 15%, about 20%, about 50%, about 75%, about 100%, or about 200%, as compared to a control; a decrease by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). Gene expression can be determined as the level of a protein or a nucleic acid (e.g., mRNA and/or cDNA), which can be detected by standard art known methods such as those described herein (e.g., as determined by PCR).

By "fragment" is meant a portion of a full-length amino acid or nucleic acid sequence (e.g., any sequence described herein). Fragments may include at least 4, 5, 6, 8, 10, 11, 12, 14, 15, 16, 17, 18, 20, 25, 30, 35, 40, 45, or 50 amino acids or nucleic acids of the full length sequence. A fragment may retain at least one of the biological activities of the full length protein.

A "gene," "target gene," "target biomarker," "target sequence," "target nucleic acid" or "target protein," as used herein, is a polynucleotide or protein of interest, the detection of which is desired. Generally, a "template," as used herein, is a polynucleotide that contains the target nucleotide sequence. In some instances, the terms "target sequence," "template DNA," "template polynucleotide," "target nucleic acid," "target polynucleotide," and variations thereof, are used interchangeably.

By "metric" is meant a measure. A metric may be used, for example, to compare the levels of a polypeptide or nucleic acid molecule of interest (e.g., any gene expressed herein). Exemplary metrics include, but are not limited to, mathematical formulas or algorithms, such as one or more ratios or one or more principal components. The metric to be used is that which best discriminates between gene expression levels in a subject having PDAC and a normal reference subject or a reference subject not having PDAC (e.g., a reference subject with pancreatitis). Depending on the metric that is used, the diagnostic indicator of PDAC may be significantly above or below a reference value. The metric can include both increased level of one or more genes to indicate PDAC or decreased level of expression of one of more genes to indicate PDAC. These levels can be expressed as one or more expression values.

By "pancreatic ductal adenocarcinoma therapy" is meant any therapy known in the art for the treatment of pancreatic ductal adenocarcinoma, such as, therapeutic agents or modalities for pancreatic cancer (e.g., erlotinib, fluorouracil, gemcitabine, mitomycin C, oxaliplatin, radiation, drugs interrupting the desmoplastic stromas, such as angiotensin receptor inhibitors, and combinations thereof).

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs.

"Response" as used herein indicates a patient's response to a pancreatic ductal adenocarcinoma therapy, e.g., a response can be a positive response such that symptoms will be alleviated and/or the risk of mortality will be reduced as a result of the pancreatic ductal adenocarcinoma therapy.

By "solid support" is meant a structure capable of storing, binding, or attaching one or more binding agents.

By "subject" is meant a mammal, including, but not limited to, a human or non-human mammal, such as a non-human primate (e.g., chimpanzee), bovine, equine, canine, ovine, or feline.

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "substantially complementary" or "substantial complement" is meant a polynucleotide sequence that has the exact complementary polynucleotide sequence, as a target nucleic acid, or has a specified percentage or nucleotides that are the exact complement at the corresponding location within the target nucleic acid when the two sequences are optimally aligned. For example, a polynucleotide sequence that is "substantially complementary" to a target nucleic acid sequence or that is a "substantial complement" to a target nucleic acid sequence has at least 50%, 60%, 70%, 75%, 80%, 85%, 90%, 95%, 96%, 97%, 98%, 99%, or 100% complementarity to the target nucleic acid sequence, or a complement thereof.

By "target sequence" is meant a portion of a gene or a gene product, including the mRNA, related cDNA, or protein encoded by the gene.

By "therapeutic agent" is meant any agent that produces a healing, curative, stabilizing, or ameliorative effect.

A "therapeutically effective amount" of a compound may vary according to factors such as the disease state, age, sex, and weight of the individual, and the ability of the compound to elicit a desired response in the individual. A therapeutically effective amount encompasses an amount in which any toxic or detrimental effects of the compound are outweighed by the therapeutically beneficial effects. A therapeutically effective amount also encompasses an amount sufficient to confer benefit, e.g., clinical benefit.

By "treating" or "ameliorating" is meant administering a composition (e.g., a pharmaceutical composition) for therapeutic purposes or administering treatment to a subject already suffering from a condition or disorder to improve the subject's condition or to reduce the likelihood of a condition or disorder. By "treating a condition or disorder" or "ameliorating a condition or disorder" is meant that the condition or disorder and/or the symptoms associated with the condition or disorder are, e.g., alleviated, reduced, cured, or placed in a state of remission. By "reducing the likelihood of" is meant reducing the severity, the frequency, and/or the duration of a disorder (e.g., PDAC) or symptoms thereof. Reducing the likelihood of PDAC is synonymous with prophylaxis or the chronic treatment of PDAC.

Other features and advantages of the invention will be apparent from the following Detailed Description and the claims.

DETAILED DESCRIPTION OF THE INVENTION

Figure 1:
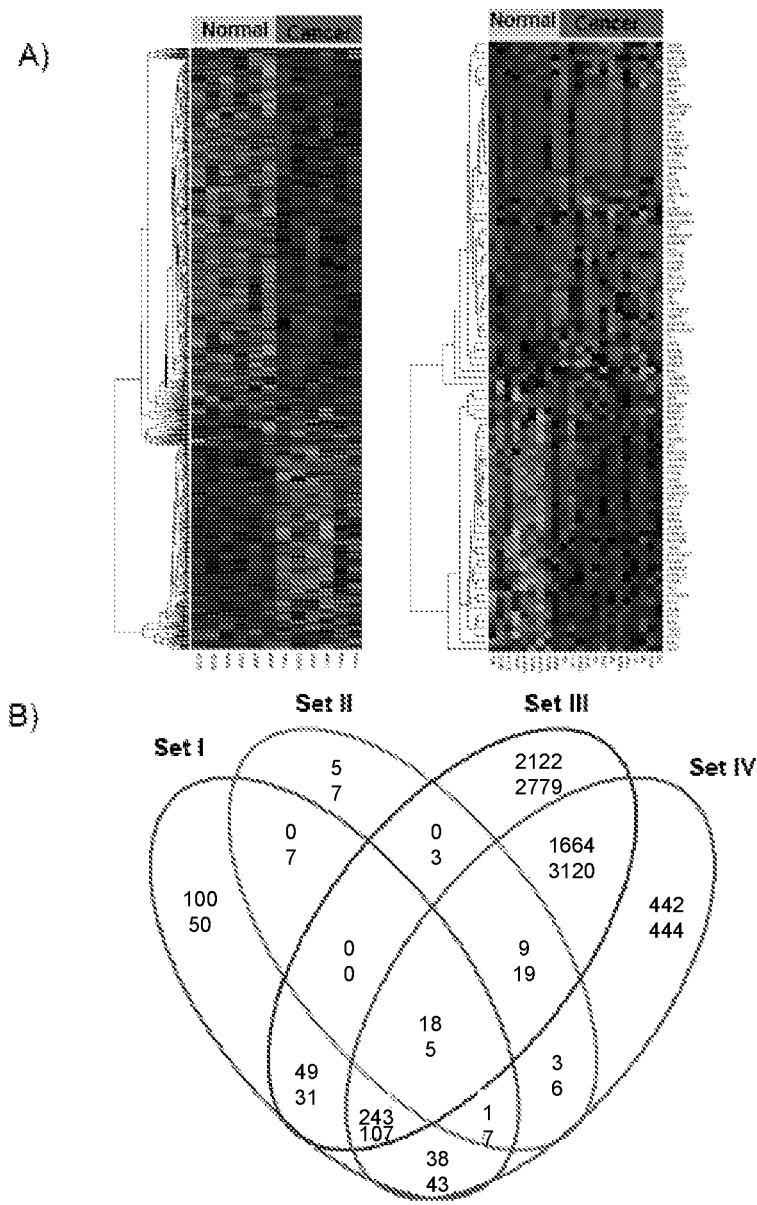
FIG. 1 is an image that illustrates the identification of significantly differentially expressed genes using empirical Bayes approach from uniformly normalized and transformed data.

The present invention relates to the identification of genes and gene combinations that are correlated with patients having or being predisposed to developing PDAC. 10-gene and 5-gene classifier panels with high sensitivity and specificity have been utilized to differentiate PDAC and early stage PDAC (e.g., IPMN) from healthy controls, as well as pancreatitis. Accordingly, the methods and kits described herein can be useful for treating or diagnosing a disease, e.g., PDAC or pancreatitis, as well as diagnostic tests (e.g., a solid support, such as an array) for performing such methods. Examples of methods and kits are described in detail below.

Genes

Genes useful in methods of the invention include:

ECT2 Epithelial Cell Transforming Sequence 2 Oncogene (ECT2)

The protein encoded by this gene is a guanine nucleotide exchange factor and transforming protein that is related to Rho-specific exchange factors and yeast cell cycle regulators. The expression of this gene is elevated with the onset of DNA synthesis and remains elevated during G2 and M phases. In situ hybridization analysis showed that expression is at a high level in cells undergoing mitosis in regenerating liver. Thus, this protein is expressed in a cell cycle-dependent manner during liver regeneration, and is thought to have an important role in the regulation of cytokinesis. Several transcript variants encoding two different isoforms have been found for this gene.

AHNAK Nucleoprotein 2 (AHNAK2)

The protein encoded by this gene is AHNAK2 a 600-kDa protein composed of a large number of highly conserved repeat segments. Structural predictions suggest that the repeat segments of AHNAK2 may have as its basic framework a series of linked, antiparallel beta-strands similar to those found in beta-propeller proteins. AHNAK2 appears to localize to Z-band regions of mouse cardiomyocytes and cosediment with membrane vesicles containing the dihydropyridine receptor, which is consistent with earlier reports that the AHNAKs are linked to L-type calcium channels and can be phosphorylated by protein kinase A. The localization of AHNAK2 in close proximity to transverse tubule membranes and Z-band regions of cardiac sarcomeres raise the possibility that they might be involved in regulating excitation/contraction coupling of cardiomyocytes, but other studies indicate that the association of AHNAKs with calcium channel proteins is more widespread. AHNAK2 is predicted to have a PDZ domain within its N-terminal, nonrepeating domain, which may mediate these interactions.

Serpin Peptidase Inhibitor, Glade B (Ovalbumin), Member 5 (SERPINB5)

The protein encoded by this gene belongs to the serpin (serine protease inhibitor) superfamily. SERPINB5 also functions as a tumor suppressor gene in epithelial cells. The expressed protein suppresses the ability of cancer cells to invade and metastasize other tissues. The protein also functions as an angiogenesis inhibitor.

Transmembrane Protease, Serine 4 (TMPRSS4)

This gene encodes a member of the serine protease family. Serine proteases are known to be involved in a variety of biological processes, whose malfunction often leads to human diseases and disorders. This gene was identified as a gene overexpressed in pancreatic carcinoma. The encoded protein is membrane bound with an N-terminal anchor sequence and a glycosylated extracellular region containing the serine protease domain. Multiple transcript variants encoding different isoforms have been found for this gene.

Periostin, Osteoblast Specific Factor (POSTN) The protein encoded by this gene functions as a ligand for alpha-V/beta-3 and alpha-V/beta-5 integrins to support adhesion and migration of epithelial cells.

S100 calcium binding protein P (S100P)

The protein encoded by this gene is a member of the S100 family of proteins containing 2 EF-hand calcium-binding motifs. S100 proteins are localized in the cytoplasm and/or nucleus of a wide range of cells, and involved in the regulation of a number of cellular processes such as cell cycle progression and differentiation. S100 genes include at least 13 members which are located as a cluster on chromosome 1 q21; however, this gene is located at 4p16. This protein, in addition to binding Ca2+, also binds Zn2+ and Mg2+. This protein may play a role in the etiology of prostate cancer.

Carcinoembryonic Antigen-Related Cell Adhesion Molecule 5 (CEACAM5)

This gene encodes a member of the carcinoembryonic antigen (CEA) gene family, which belongs to the immunoglobulin superfamily. Two subgroups of the CEA family, the CEA cell adhesion molecules and the pregnancy-specific glycoproteins, are located within a 1.2 Mb cluster on the long arm of chromosome 19. Eleven pseudogenes of the CEA cell adhesion molecule subgroup are also found in the cluster. The encoded protein mediates cell adhesion via homophilic as well as heterophilic binding to other proteins of the subgroup. Multiple cellular activities have been attributed to the encoded protein, including roles in the differentiation and arrangement of tissue three-dimensional structure, angiogenesis, apoptosis, tumor suppression, metastasis, and the modulation of innate and adaptive immune responses. Multiple transcript variants encoding different isoforms have been reported, but the full-length nature of all variants has not been defined.

Gamma-Aminobutyric Acid (GABA) a Receptor, Pi (GABRP)

The gamma-aminobutyric acid (GABA) A receptor is a multisubunit chloride channel that mediates the fastest inhibitory synaptic transmission in the central nervous system. The subunit encoded by this gene is expressed in several non-neuronal tissues including the uterus and ovaries. This subunit can assemble with known GABA A receptor subunits, and the presence of this subunit alters the sensitivity of recombinant receptors to modulatory agents such as pregnanolone.

Chymotrypsin-Like Elastase Family, Member 2B (CELA2B)

Elastases form a subfamily of serine proteases that hydrolyze many proteins in addition to elastin. Humans have six elastase genes which encode the structurally similar proteins elastase 1, 2, 2A, 2B, 3A, and 3B. Like most of the human elastases, elastase 2B is secreted from the pancreas as a zymogen. In other species, elastase 2B has been shown to preferentially cleave proteins after leucine, methionine, and phenylalanine residues.

CUB and Zona Pellucida-Like Domains 1 (CUZD1)

The protein encoded by this gene may play a role in cell attachment and proliferation.

Diagnostic Methods

The present invention features methods and compositions to diagnose PDAC and monitor the progression of such a disorder. The methods of the invention may be used as a companion diagnostic with other diagnostic approaches (e.g., EUS FNA), as early molecular screening to distinguish benign pancreatic cysts, pancreatitis, or other forms of pancreatic cancer from pancreatic ductal adenocarcinoma, and/or classify different stages of pancreatic ductal adenocarcinoma. For example, the methods can include determining an expression level of one or more genes in a biological sample and comparing the level to a normal reference. The expression level of a gene, e.g., any described herein, can be determined by one or more of mRNA expression level, cDNA expression level, or protein expression level. These genes and their gene products can also be used to monitor the therapeutic efficacy of compounds, including therapeutic agents described herein, used to treat PDAC or a related disorder (e.g., pancreatitis).

Alterations in the expression or biological activity of one or more genes of the invention in a test sample as compared to a normal reference can be used to diagnose PDAC or a related disease (e.g., pancreatitis) and/or distinguish PDAC from benign non-malignant pancreatic aberrations such as pancreatitis and benign pancreatic cysts.

Expression of various genes or biomarkers in a sample can be analyzed by a number of methodologies, many of which are known in the art and understood by the skilled artisan, including but not limited to, immunohistochemical and/or western blot analysis, immunoprecipitation, molecular binding assays, ELISA, ELIFA, fluorescence activated cell sorting (FACS), mass spectrometry, quantitative blood based assays (as for example serum ELISA) (to examine, for example, levels of protein expression), biochemical enzymatic activity assays, in situ hybridization, northern analysis and/or PCR analysis of mRNAs, as well as any one of the wide variety of assays that can be performed by gene and/or tissue array analysis or sequencing. Typical protocols for evaluating the status of genes and gene products are found, for example in Ausubel et al. eds., 1995, Current Protocols In Molecular Biology, Units 2 (Northern Blotting), 4 (Southern Blotting), 15 (Immunoblotting), and 18 (PCR Analysis). Multiplexed immunoassays such as those available from Rules Based Medicine or Meso Scale Discovery (MSD), Multiple Reaction Monitoring (MRM), multiplexed RTPCR, IHC or multiplex variation of any of the above-mentioned assays may also be used.

A sample comprising a target gene or biomarker can be obtained by methods well known in the art. For instance, samples from a subject may be obtained by venipuncture, resection, bronchoscopy, fine needle aspiration, bronchial brushings, or from sputum, pleural fluid, urine or blood, such as serum or plasma. Genes or gene products (e.g., mRNA, cDNA, or protein) can be detected from these samples. By screening such body samples, a simple early diagnosis or differential diagnosis can be achieved for PDAC or related diseases. In addition, the progress of therapy can be monitored more easily by testing such body samples for target genes or gene products. Furthermore, the prediction of outcome or response to therapy can be tested more easily by testing such body samples for target genes or gene products.

In certain embodiments, the expression of a protein of one or more genes in a sample is examined using immunohistochemistry ("IHC") and staining protocols. IHC staining of tissue sections has been shown to be a reliable method of assessing or detecting presence of proteins in a sample. IHC and IFC techniques use an antibody to probe and visualize cellular antigens in situ, generally by chromogenic or fluorescent methods. The tissue sample may be fixed (i.e., preserved) by conventional methodology (see, e.g., "Manual of Histological Staining Method of the Armed Forces Institute of Pathology," 3$^{rd}$ edition (1960) Lee G. Luna, HT (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the sample is to be histologically stained or otherwise analyzed. By way of example, neutral buffered formalin, Bouin's or paraformaldehyde, may be used to fix a sample. Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. The primary and/or secondary antibody used for immunohistochemistry typically will be labeled with a detectable moiety, such as a radioisotope, a colloidal gold particle, a fluorescent label, a chromogenic label, or an enzyme-substrate label.

In alternative methods, the sample may be contacted with an antibody specific for the gene or biomarker under conditions sufficient for an antibody-biomarker complex to form, and then detecting the complex. The presence of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279, and 4,018,653. These include both single-site and two-site or "sandwich" assays of the noncompetitive types, as well as in the traditional competitive binding assays. These assays also include direct binding of a labeled antibody to a target biomarker.

Another method involves immobilizing the target biomarkers (e.g., on a solid support) and then exposing the immobilized target to specific antibody, which may or may not contain a label. Depending on the amount of target and the strength of the label's signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by a label, e.g., an enzyme, a fluorescent label, a chromogenic label, a radionuclide containing molecule (i.e., a radioisotope), or a chemiluminescent molecule.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface (e.g., a glass or a polymer surface, such as those with solid supports in the form of tubes, beads, discs, or microplates), and a second antibody is linked to a label that is used to indicate the binding of the second antibody to the molecular marker.

Another methodology for determining expression level in a sample is in situ hybridization, for example, fluorescence in situ hybridization (FISH) (see, e.g., Angerer et al., *Methods Enzymol.* 152:649-661, 1987). Generally, in situ hybridization includes the following steps: (1) fixation of a biological sample to be analyzed; (2) pre-hybridization treatment of the biological sample to increase accessibility of target DNA and to reduce non-specific binding; (3) hybridization of the mixture of nucleic acids to the nucleic acid in the biological sample; (4) post-hybridization washes to remove nucleic acid fragments not bound in the hybridization; and (5) detection of the hybridized nucleic acid fragments. The binding agents (e.g., probes) used in such applications are typically labeled, for example, with radioisotopes or fluorescent labels. Preferred probes are sufficiently long, for example, from about 50, 100, or 200 nucleotides to about 1000 or more nucleotides, to enable specific hybridization with the target nucleic acid(s) under stringent conditions.

Another methodology for determining expression level in a sample is Immuno-PCR (IPCR). IPCR employs conjugates between nucleic acid marker sequences and antibodies together with PCR, which is widely applied for detecting various types of targets including proteins (see Sano et al., Science 258 pp: 120-122(1992), U.S. Pat. No. 5,665,539, Niemeyer et al., Trends in Biotechnology 23 pp: 208-216 (2005), U.S. Pat. Pub. No. 2005/0239108 and Ye et al., Journal of Environmental Science 22 pp: 796-800(2010)).

Alternative methods for determining the expression level in a sample include bead based multiplex assays, such as Luminex, and multiple reaction monitoring (MRM) mass spectrometry based assays.

Amplification-based assays also can be used to measure the expression level of one or more genes. In such assays, the nucleic acid sequences of the gene act as a template in an amplification reaction (for example, a polymerase chain reaction (PCR) or quantitative PCR). In a quantitative amplification, the amount of amplification product will be proportional to the amount of template in the original sample. Comparison to appropriate controls provides a measure of the expression level of the gene, corresponding to the specific probe used, according to the principles discussed above. Methods of real-time quantitative PCR using TaqMan probes are well known in the art. Detailed protocols for real-time quantitative PCR are provided, for example, in Gibson et al., *Genome Res.* 6:995-1001, 1996, and in Heid et al., *Genome Res.* 6:986-994, 1996.

Based on the sequences of the genes provided herein, one of skill in the art would be able to use these sequences to design and construct primers that can specifically bind to the mRNA or cDNA sequence in order to perform an amplification-based assay. Any useful program can be used to design primers, such as Primer Premier (available by Premier Biosoft International, Palo Alto, Calif.), Primer-Blast (available at www.ncbi.nlm.nih.gov/tools/primer-blast/by NCBI), Primer3 (available at biotools.umassmed.edu/bioapps/primer3_www.cgi), and OligoAnalyzer (available at www.idtdna.com/SciTools/SciTools.aspx by Integrated DNA Technologies, Inc., San Diego, Calif.).

A TaqMan-based assay also can be used to quantify expression level. TaqMan-based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, for example, AmpliTaq, results in the cleavage of the TaqMan probe. This cleavage separates the 5' fluorescent dye and the 3' quenching agent, thereby resulting in an increase in fluorescence as a function of amplification.

Other suitable amplification methods include, but are not limited to, ligase chain reaction (LCR) (see, e.g., Wu and Wallace, *Genomics* 4:560-569, 1989; Landegren et al., *Science* 241: 1077-1080, 1988; and Barringer et al., *Gene* 89:117-122, 1990), transcription amplification (see, e.g., Kwoh et al., *Proc. Natl. Acad. Sci. USA* 86:1173-1177, 1989), self-sustained sequence replication (see, e.g., Guatelli et al., *Proc. Natl. Acad. Sci. USA* 87:1874-1878, 1990), dot PCR, and linker adapter PCR.

Expression levels may also be determined using microarray-based platforms (e.g., single-nucleotide polymorphism (SNP) arrays), as microarray technology offers high resolution. Details of various microarray methods can be found in the literature. See, for example, U.S. Pat. No. 6,232,068 and Pollack et al., *Nat. Genet.* 23:41-46, 1999.

Methods of the invention further include protocols which examine the presence and/or expression of mRNAs of one or more genes, in a tissue or cell sample. Methods for the evaluation of mRNAs in cells are well known and include, for example, hybridization assays using complementary DNA probes (such as in situ hybridization using labeled riboprobes specific for the one or more genes, northern blot and related techniques) and various nucleic acid amplification assays (such as RT-PCR using complementary primers specific for one or more of the genes, and other amplification type detection methods, such as, for example, branched DNA, SISBA, TMA, and the like).

Tissue or cell samples from mammals can be conveniently assayed for mRNAs using Northern, dot blot or PCR analysis. For example, RT-PCR assays such as quantitative PCR assays are well known in the art. In an illustrative embodiment of the invention, a method for detecting a target mRNA in a biological sample comprises producing cDNA from the sample by reverse transcription using at least one primer; amplifying the cDNA so produced using a target polynucleotide as sense and antisense primers to amplify target cDNAs therein; and detecting the presence of the amplified target cDNA using polynucleotide probes. In some embodiments, primers and probes comprising the sequences described herein are used to detect expression of one or more genes, as described herein. In addition, such methods can include one or more steps that allow one to determine the levels of target mRNA in a biological sample (e.g., by simultaneously examining the levels a comparative control mRNA sequence of a "housekeeping" gene such as an actin family member or any control gene described herein, such as GAPDH). Optionally, the sequence of the amplified target cDNA can be determined.

Optional methods of the invention include protocols which examine or detect mRNAs, such as target mRNAs, in a tissue or cell sample by microarray technologies. Using nucleic acid microarrays, test and control mRNA samples from test and control tissue samples are reverse transcribed and labeled to generate cDNA probes. The probes can then hybridized to an array of nucleic acids immobilized on a solid support. The array can be configured such that the sequence and position of each member of the array is known. For example, a selection of genes whose expression correlate with the presence of PDAC, an increased likelihood of developing PDAC, or increased severity of PDAC can be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment, (see, e.g., WO 01/75166 published Oct. 11, 2001; (see, for example, U.S. Pat. Nos. 5,700,637, 5,445,934, and 5,807,522, Lockart, *Nat. Biotechnol.* 14:1675-1680 (1996); Cheung et al., *Nat. Genet.* 21(Suppl):15-19 (1999) for a discussion of array fabrication).

DNA microarrays are miniature arrays containing gene fragments that are either synthesized directly onto or spotted onto glass or other substrates. Thousands of genes are usually represented in a single array. A typical microarray experiment involves the following steps: 1) preparation of fluorescently labeled target from RNA isolated from the sample, 2) hybridization of the labeled target to the microarray, 3) washing, staining, and scanning of the array, 4) analysis of the scanned image and 5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ). Commercially available microarray systems can be used, such as the Affymetrix GeneChip® system.

Next Generation sequencing methods may be used with the methods of the invention. Next generation sequencing methods are sequencing technologies that parallelize the sequencing process, producing thousands or millions of sequences concurrently (see, for example, Hall, *J. Exp. Biol.* 209(Pt.9):1518-1525 (2007) for a review of next generation methods). Next generation sequencing methods include, but are not limited to, polony sequencing, 454 pyrosequencing, Illumina (Solexa) sequencing, SOLiD sequencing, Ion Torrent semiconductor sequencing, DNA nanoball sequencing, Heliscope single molecule sequencing, single molecule real time sequencing, nanopore DNA sequencing (see, for example, Dela Torre et al. *Nanotechnology,* 23(38):385308, 2012), tunneling currents DNA sequencing (see, for example, Massimiliano, *Nanotechnology,* 24:342501, 2013), sequencing by hybridization (see, for example, Qin et al. *PLoS One,* 7(5):e35819, 2012), sequencing with mass spectrometry (see, for example, Edwards et al. *Mutation Research,* 573(1-2):3-12, 2005), microfluidic Sanger sequencing (see, for example, Kan et al. *Electrophoresis,* 25(21-22):3564-3588, 2004), microscopy-based sequencing (see, for example, Bell et al. *Microscopy and microanalysis: the official journal of Microscopy Society of America, Microbeam Analysis Society, Microscopical Society of Canada,* 18(5):1-5, 2012), and RNA polymerase sequencing (see, for example, Pareek et al. *J. Applied Genetics,* 52(4):413-415, 2011).

Polony sequencing combines an in vitro paired-tag library with emulsion PCR, an automated microscope, and ligation-based sequencing chemistry (see, for example, Shendure et al. *Science,* 309(5741):1728-1732, 2005).

454 pyrosequencing utilizes emulsion PCR with each droplet containing a single DNA template attached to a single primer-coated bead that then forms a clonal colony. The instrument contains many picoliter wells each containing a single bead and sequencing enzymes, and utilizing luciferase to generate light for detection of the individual nucleotides added to the DNA (see, for example, Margulies et al. *Nature,* 437(7057):376-380, 2005).

Illumina sequencing is based on reversible dye-terminators technology, and engineered polymerases. DNA molecules and primers are attached on a slide and amplified with polymerase to form DNA clusters. The sequence is determine by addition of four types of reversible terminator bases, and washing away of non-incorporated nucleotides. Fluorescently labeled nucleotides are imaged, then the dye and terminal 3' blocker are chemically removed, allowing the next cycle to begin (see, for example, Mardis *Ann. Rev. Genomics Hum. Genet.* 9:387-402, 2008).

SOLiD sequencing employs sequencing by ligation. A pool of all possible oligonucleotides of a fixed length are labeled according to the sequenced position. Oligonucleotides are annealed and ligated, and the DNA is amplified by emulsion PCR. The beads are deposited on a glass slide (see, for example, Valouev et al. *Genome Res.* 18(7):1051-1063, 2008).

Ion torrent semiconductor sequencing employs standard sequencing chemistry with a semiconductor based detection system to detect hydrogen ions that are released during polymerization of DNA (see, for example, Rusk *Nat. Meth.,* 8(1):44, 2011). Microwells containing a template DNA strand are flooded with a single type of nucleotide. If the introduced nucleotide is complementary, it is incorporated into the growing complementary strand. This incorporation results in the release of a hydrogen ion that is detected by the sensor, indicating that a reaction has occurred.

DNA nanoball sequencing utilizes rolling circle replication to amplify fragments of genomic DNA into DNA nanoballs. Unchained sequencing by ligation is then used to determine the nucleotide sequence (see, for example, Drmanac et al, *Science,* 327(5961):78-81, 2010).

Heliscope single molecule sequencing utilizes DNA fragments with poly-A tail adapters attached to a flow cell surface. Extension-based sequencing with cyclic washes of the flow cell with fluorescently labeled nucleotides are then performed (see, for example, Thompson et al. *Current Protocols in Molecular Biology*, Chapter 7, 2010).

Expression of a selected gene or biomarker in a tissue or cell sample may also be examined by way of functional or activity-based assays. For instance, if the biomarker is an enzyme, one may conduct assays known in the art to determine or detect the presence of the given enzymatic activity in the tissue or cell sample.

Any of the methods herein can be adapted to include a solid support. Exemplary solid supports include a glass or a polymer surface, including one or more of a well, a plate, a wellplate, a tube, an array, a bead, a disc, a microarray, or a microplate. In particular, the solid supported can be adapted to allow for automation of any one of the methods described herein (e.g., PCR). Alternatively microfluidics or microdroplets could be used.

Detection of amplification, overexpression, or overproduction of, for example, a gene or gene product can also be used to provide prognostic information or guide therapeutic treatment. Such prognostic or predictive assays can be used to determine prophylactic treatment of a subject prior to the onset of symptoms of, e.g., PDAC or a related disease (e.g., pancreatitis) or stratification of patients to particular treatment protocols.

The diagnostic methods described herein can be used individually or in combination with any other diagnostic method described herein for a more accurate diagnosis of the presence or severity of a disorder (e.g., PDAC or a related disorder). Examples of additional methods for diagnosing such disorders include, e.g., examining a subject's health history, immunohistochemical staining of tissues, or performing one or more laboratory tests, such as testing for elevated conjugated bilirubin, gamma-glutamyl transpeptidase, alkaline phosphatase, or CA19-9 levels, imaging tests (e.g., computed tomography (i.e. CT scan), endoscopic ultrasound (i.e., EUS)), endoscopic needle biopsy, or surgical excision of tissue.

Binding Agent

A binding agent that specifically binds a target gene or a gene product (e.g., mRNA, cDNA, or protein) may be used for the diagnosis of a disease, such as PDAC. The binding agent may be, e.g., a protein (e.g., an antibody, antigen, or fragment thereof), a polynucleotide, a small molecule, or a peptdomimetic. The polynucleotide may possess sequence specificity for the gene (e.g., as in a primer) or may be an aptamer.

Based on the genes provided herein, one of skill in the art would be able to use these sequences to design and construct binding agents that can specifically bind to the mRNA, cDNA, or protein sequence. For example, the particular sequence for a gene is provided in the UniGene database, where accession numbers for each gene are provided herein. Any useful program can be used to input a sequence and design primers, such as Primer Premier (available by Premier Biosoft International, Palo Alto, Calif.), Primer-Blast (available at www.ncbi.nlm.nih.gov/tools/primer-blast/by NCBI), Primer3 (available at biotools.umassmed.edu/bio-apps/primer3 www.cgi), and OligoAnalyzer (available at www.idtdna.com/SciTools/SciTools.aspx by Integrated DNA Technologies, Inc., San Diego, Calif.).

Preferably, each binding agent specifically binds to a particular gene or gene product (e.g., mRNA, cDNA, or protein). For determining an expression level of a protein, the measurement of antibodies specific to a polypeptide of the invention (i.e., a protein product of any of the genes of the invention, such as described herein) in a subject may be used for the diagnosis of PDAC or a propensity to develop the same. Antibodies specific to one or more polypeptides of the invention (or a particular sequence for a protein provided in the UniGene database, where accession numbers for each gene is provided herein) may be measured in any bodily fluid, including, but not limited to, urine, blood, serum, plasma, saliva, pancreatic, or cerebrospinal fluid. ELISA or MRM assays are the preferred methods for measuring levels of polypeptides in a bodily fluid.

For determining an expression level of mRNA or cDNA, polynucleotides that hybridize to a gene of the invention at high stringency may be used as a probe to monitor expression levels. Methods for detecting such levels are standard in the art, such as Northern blotting, Western blotting, florescent in situ hybridization, reverse transcription PCR, (SAGE) serial analysis of gene expression (see, for example, Hanriot et al. *BMC Genomics,* 9:418, 2008), DNA microarray (see, for example, Wheelan et al. *Mol. Biosyst.,* 4(7): 726-732, 2008), Tiling arrays (see, for example, Miyakoshi et al., *BMC Genomics,* 10:12, 2009), and RNA-Seq (see, for example, Denoeud et al. *Genome BioL,* 9(12):R175, 2008). Binding can be determined at various stringency conditions, such as at high stringency conditions. The specificity of the probe, whether it is made from a highly specific region, e.g., the 5' regulatory region, or from a less specific region, e.g., a conserved motif, and the stringency of the hybridization or amplification (maximal, high, intermediate, or low), determine whether the probe hybridizes to a naturally occurring sequence, allelic variants, or other related sequences.

The binding agent may optionally contain a label, such as a radioisotope, a colloidal gold particle, a fluorescent label, a chromogenic label, an enzyme-substrate label, or a chemiluminescent label.

Methods for Predicting Response to Pancreatic Ductal Adenocarcinoma Therapies

The invention features methods for predicting response to a pancreatic ductal adenocarcinoma therapy in a subject with pancreatic ductal adenocarcinoma before or after one or more pancreatic ductal adenocarcinoma therapy, by collecting a sample, e.g., a blood or plasma sample from a subject; measuring the level of expression of a panel of at least two genes described herein, in the sample, relative to a control sample; and making a prediction whether the patient will be responsive to a pancreatic ductal adenocarcinoma therapy. The method can be used to predict whether a subject, who has been diagnosed with pancreatic ductal adenocarcinoma, will respond positively to a pancreatic ductal adenocarcinoma therapy such as a therapeutic or combination of therapeutics which target a gene product of any of the genes described herein.

A prediction of a positive response refers to a case where the pancreatic ductal adenocarcinoma symptoms will be alleviated and/or the risk of mortality will be reduced as a result of the pancreatic ductal adenocarcinoma therapy.

In the methods of predicting response to a pancreatic ductal adenocarcinoma therapy, the expression level of the gene(s) can be determined relative to a control sample. A control sample can be a sample from a normal subject, or a sample from a patient who has undergone a pancreatic ductal adenocarcinoma therapy and has reduced symptoms after the therapy.

The methods of the invention can be used to predict whether a subject will be responsive to a pancreatic ductal adenocarcinoma therapy, for example an increase in the level of expression (e.g., an increase of 20%, 30%, 50%, 80%, 100%, 200%, 300%, 500%, 800%, 1000%) of the gene(s) may indicate a positive response to a pancreatic ductal adenocarcinoma therapy. Alternatively, a decrease in the level of expression (e.g., a decrease of 20%, 30%, 50%, 80%, 100%, 200%, 300%, 500%, 800%, 1000%) of the gene(s) may indicate a poor response to a pancreatic ductal adenocarcinoma therapy.

The methods of the invention can be used to predict a patient's response to a pancreatic ductal adenocarcinoma therapy and classify the subject as a "responder", e.g., a patient with gene expression levels indicative of a positive response to a pancreatic ductal adenocarcinoma therapy, or a "non-responder", e.g. a patient with gene expression levels indicative of a poor response to pancreatic ductal adenocarcinoma therapy.

The prediction can be made prior to a first pancreatic ductal adenocarcinoma therapy. Alternatively, the prediction can be made after the first pancreatic ductal adenocarcinoma therapy, or after a first pancreatic ductal adenocarcinoma therapy but before a second pancreatic ductal adenocarcinoma therapy. Furthermore, the prediction can be made at any time during the course of a pancreatic ductal adenocarcinoma therapy.

The methods of the invention may also include collecting nucleic acid molecules from a sample, e.g., a blood or a plasma sample from a subject. The methods of the invention may include amplifying the nucleic acid molecules using, e.g., polymerase chain reaction (PCR), to produce an amplified solution. Alternatively, the methods of the invention may include measuring expression of the genes using unamplified nucleic acid molecules and Nanostring digital quantification of single molecules. The methods of the invention may further include performing qRT-PCR in a thermal cycler using the nucleic acid molecules collected from a sample or using the amplified solution described above to measure the level of expression of a biomarker in the sample. Procedures for performing qRT-PCR are described in, e.g., U.S. Pat. No. 7,101,663 and U.S. Patent Application Nos. 2006/0177837 and 2006/0088856, each of which is incorporated herein by reference. Alternatively, sequencing or other methods known in the art for measuring gene expression could be used.

Methods of Treatment

The invention features a method for treatment of pancreatic ductal adenocarcinoma in a subject by contacting a biological sample from the subject with one or more binding agents capable of specifically binding one or more genes or a protein encoded by said one or more genes; determining if the expression level of a panel of at least two genes in said biological sample is changed relative to a control sample; predicting a response to a pancreatic ductal adenocarcinoma therapy in said subject based on the level of expression of one or more of said genes; and if the prediction is positive administering a pancreatic ductal adenocarcinoma therapy.

The methods, compositions, and diagnostic tests can be used to determine the proper dosage (e.g., the therapeutically effective amount) of a therapeutic agent or to determine the proper type of therapeutic agent to administer to the subject.

Any therapeutic agent or combination of agents can be used to treat the subject having, or having a predisposition to, PDAC or a related disease (e.g., pancreatitis). Several therapeutic agents have been used in the treatment of PDAC; these include, without limitation, erlotinib, fluorouracil, gemcitabine, mitomycin C, oxaliplatin, and combinations thereof. Therapies which target gene products of any of the genes described herein or a combination thereof may be used in the treatment of subject. For example, the pancreatic ductal adenocarcinoma therapy may include administering a therapeutic agent that targets the gene product of any one of epithelial cell transforming sequence 2 oncogene (ECT2); AHNAK nucleoprotein 2 (AHNAK2); serpin peptidase inhibitor, Glade B (ovalbumin) member 5 (SERPINB5); transmembrane protease, serine 4 (TMPRSS4); periostin, osteoblast specific factor (POSTN); S100 calcium binding protein P (S100P); carcinoembryonic antigen-related cell adhesion molecule 5 (CEACAM5); gamma-aminobutyric acid (GABA) A receptor, pi (GABRP); chymotrypsin-like elastase family, member 2B (CELA2B); or CUB and zona pellucid-like domains 1 (CUZD1), a combination of two or more such therapeutic agents, or combinations of one such therapeutic with other therapeutic agents or modalities for pancreatic cancer, such as, erlotinib, fluorouracil, gemcitabine, mitomycin C, oxaliplatin, radiation, drugs interrupting the desmoplastic stromas, such as angiotensin receptor inhibitors, and combinations thereof.

Diagnostic Kits

The invention also provides for a diagnostic test kit. For example, a diagnostic test kit can include one or more binding agents (e.g., polynucleotides, such a primers or probes, or polypeptides, such as antibodies), and components for detecting, and more preferably evaluating binding between the binding agent (e.g., a primer, a probe, or an antibody) and a gene or gene product of the invention. In another example, the kit can include a polynucleotide or polypeptide for a gene of the invention, or fragment thereof, for the detection of mRNA or antibodies in the serum or blood of a subject sample that bind to the polynucleotide or polypeptide of the invention. For detection, one or more of the polynucleotide, antibody, or the polypeptide is labeled. In further embodiments, one or more of the polynucleotide, antibody, or the polypeptide is substrate-bound, such that the polypeptide-antibody or polynucleotide-mRNA interaction can be established by determining the amount of label attached to the substrate following binding between the antibody and the polypeptide. A conventional ELISA is a common, art-known method for detecting antibody-substrate interaction and can be provided with the kit of the invention. For detecting the polynucleotide-mRNA interaction, known amplification-based assays can be conducted, such as PCR.

The kit can be used to detect expression level in virtually any bodily fluid, such as urine, plasma, blood serum, semen, saliva, pancreatic or cerebrospinal fluid. A kit that determines an alteration in the level of a polypeptide of the invention relative to a reference, such as the level present in a normal control, is useful as a diagnostic kit in the methods of the invention. Such a kit may further include a reference sample or standard curve indicative of a positive reference or a normal control reference.

Desirably, the kit will contain instructions for the use of the kit. In one example, the kit contains instructions for the use of the kit for the diagnosis of PDAC or a propensity to develop the same. In yet another example, the kit contains instructions for the use of the kit to monitor therapeutic treatment or dosage regimens. In yet another example, the kit contains instructions for the use of the kit to predict outcome, response to therapy or disease recurrence. In a further example, the instructions include one or more metrics.

Screening Assays

As discussed above, we have discovered that the expression level of one or more genes is involved in PDAC. Based on these discoveries, one or more of these genes (e.g., ECT2) are useful for the high-throughput low-cost screening of candidate compounds to identify those that modulate, alter, or decrease (e.g., by at least 10%, 20%, 30%, 40%, 50%, 60%, 70%, 80%, 90%, 95%, or more), the expression or biological activity of one or more of these genes or the gene product.

These genes are shown to be up or down regulated by the expression level of the gene or the gene product. Compounds that decrease the expression or biological activity of an activated gene of the invention (e.g., ECT2, AHNAK2, SERPINB5, TMPRSS4, POSTN, S100P, CEACAM5, or GABRP) can be used for the treatment or prevention of PDAC or a related disorder (e.g., pancreatitis). Compounds that decrease the expression or biological activity of an upregulated gene of the invention (e.g., ECT2, AHNAK2, SERPINB5, TMPRSS4, POSTN, S100P, CEACAM5, or GABRP) can also be used for the treatment or prevention of PDAC or a related disorder (e.g., pancreatitis) as well as other cancers and diseases where expression or activity of any of these genes is altered.

In general, candidate compounds are identified from large libraries of both natural product or synthetic (or semi-synthetic) extracts, chemical libraries, or from polypeptide (e.g., antibody) or nucleic acid libraries, according to methods known in the art. Those skilled in the field of drug discovery and development will understand that the precise source of test extracts or compounds is not critical to the screening procedure(s) of the invention. Alternatively, 3D structures of the proteins can be used for in silico high throughput docking of small molecules into the proteins to identify molecules that specifically interact with a particular protein.

Subject Monitoring

The diagnostic methods described herein can also be used to monitor PDAC or a related disease (e.g., pancreatitis) during therapy or to determine the dosage of one or more therapeutic agents. For example, alterations (e.g., an increase or a decrease as compared to the positive reference sample or level for PDAC) can be detected to indicate an improvement of the symptoms of PDAC. In this embodiment, the levels of the polypeptide, nucleic acid, or antibodies are measured repeatedly as a method of not only diagnosing disease but also monitoring the treatment, prevention, or management of the disease.

In order to monitor the progression of PDAC in a subject, subject samples are compared to reference samples taken early in the diagnosis of the disorder. Such monitoring may be useful, for example, in assessing the efficacy of a particular therapeutic agent in a subject, determining dosages, or in assessing disease progression or status. For example, levels of ECT2, AHNAK2, SERPINB5, TMPRSS4, POSTN, S100P, CEACAM5, GABRP, CELA2B, or CUZD1 or any combination thereof, can be monitored in a patient having PDAC and as the levels or activities increase or decrease, relative to control, the dosage or administration of therapeutic agents may be adjusted.

EXAMPLES

The following examples are intended to illustrate the invention. They are not meant to limit the invention in any way.

Materials and Methods

Meta-Analysis to Identify Optimal PDAC Biomarker Panel

The plethora of published potential PDAC biomarkers was refined to a small set of the most promising candidates by employing an optimized meta-analysis strategy.

Dataset Identification

The literature and publicly available microarray repositories (ArrayExpress, Gene Expression Omnibus (GEO), ONCOMINE, and Stanford Microarray Database [SMD]) were searched for gene expression studies of human PDAC specimens. Identified datasets were divided into training sets (a minimum of four samples of normal pancreas (NP) compared to a minimum of four samples of PDAC) and validation sets.

Cross-Platform GeneID Annotation

To facilitate the collation of the differentially expressed genes identified by analyses of individual datasets, the probe-level identifiers associated with each dataset were annotated with corresponding gene-level identifiers. GeneIDs were used in all subsequent analyses to map genes across the datasets to avoid ambiguity from non-unique gene identifiers. For Affymetrix GeneChip data, Affymetrix probe set IDs were annotated using the appropriate microarray chip annotation package (http://www.bioconductor.org/packages/release/AffymetrixChip.html) and the annotated package (http://www.bioconductor.org/packages/2.4/bioc/html/annotate.html) available through Bioconductor. Because each human Entrez Gene ID (GeneID) is unique to a single gene and each gene can only map to one GeneID, the four lists of differentially expressed genes were combined using the GeneIDs that correspond to the probe IDs specific to a given microarray platform. Affymetrix probe set IDs that could not be mapped to an Entrez Gene ID (GeneID) were removed from the gene lists.

Pre-Processing of Microarray Data

Potential bias introduced by the range of methodologies used in the original microarray studies, including various experimental platforms and analytic methods, was controlled by applying the same simple global normalization and filtering strategy to each dataset. As previously implemented for successful meta-analysis of diverse microarray datasets, the gene expression values of each microarray corresponding to a single sample in a given dataset are normalized to a median of zero and a standard deviation of one.

Each Affymetrix dataset was normalized from raw data (.cel files), when available, using the Frozen RMA (fRMA) algorithm with rma background correction implemented through functions provided by the Bioconductor package affy. Frozen RMA (fRMA) is a microarray-preprocessing algorithm that utilizes information from large publicly available microarray databases to pre-compute and freeze estimates of probe-specific effects and variances. The frozen fRMA data is updated with information from new array datasets to provide a normalized summary of the combined data. When the probe-level data contained in .cel files was not available, we used the gene expression data matrix (GEDM) of Affymetrix average difference intensities. The normalized datasets were preprocessed using the Z-statistics normalization to reduce the batch effects among different datasets.

Differential Expression Analysis

For training set differential expression analysis, the two sample classes were normal pancreas (NP) and PDAC and the null hypothesis was "no difference in gene expression exists between the NP and PDAC sample classes". Empirical Bayes moderated t-statistic for differential expression analysis minimizes the effects of small sample numbers and has been shown to perform well across microarray datasets with a range of sample sizes. Accordingly, for each probe in each dataset, we computed the empirical Bayes moderated t-statistic and the corresponding p-value using the Bioconductor package Limma. Differentially expressed genes are defined as a limma p-value less than 0.05 (with Benjamini and Hochberg method for multiple comparison correction to control false discovery rate [FDR]) and an absolute value of log fold change (FC) of at least 0.6 (corresponds to a FC of approximately 1.5). This statistical testing procedure for differential gene expression analysis of microarray data controls for false positive results, a critical issue arising from the simultaneous testing of tens of thousands of genes. Thus, potential genes for inclusion in the biomarker panel to distinguish PDAC from normal pancreas tissue had differential expression in at least two of the four training sets, corresponding to a false discovery rate (FDR) of <10%.

The genes that were found to be differentially expressed and with concordant directionality (upregulation or downregulation) in three out of four datasets were used for generating the PDAC classifier. Relative gene expression levels in PDAC compared to normal pancreas were visualized with standard heatmaps and Venn diagrams, with the extent of overexpression or underexpression denoted by red or blue shading, respectively. Fold change was calculated from the mean difference (base-two log-transformed mean expression of PDAC samples—base-two log-transformed mean expression of NP samples) values extracted for each gene from each dataset during data collation.

Class Prediction Analysis of Biomarker Candidates

The intersect matrix of the four gene lists resulting from the analysis of individual datasets was computed using Bioconductor packages. The top 40 differentially expressed genes on the basis of cumulative rank in four lists were selected. The classifier was built by implementing Support Vector Machines (SVM) using freely available packages in Bioconductor. Classifiers were trained against a dataset constructed from the normalized base-two log transformed expression values for each significant differentially expressed gene identified by our primary meta-analysis across all samples in each dataset. Potential biomarker panels containing a varying number of genes generated by the class prediction analysis were evaluated for performance using leave one out cross-validation (LOOCV).

The biomarker panels with the highest sensitivity and specificity in the training sets were chosen for assessment of predictive power in 9 independent validation datasets using thresholds-dependent (e.g. sensitivity, specificity, and accuracy) and threshold-independent (area under curve) measures.

Assessment of Potential Bias

To determine whether individual study bias significantly influenced gene expression values, we examined the major similarities and differences with principal component analysis (PCA). PCA is a data reduction technique that allows high-dimensional datasets, such as microarray datasets, to be plotted by representing the data using relatively few principal components that reflect directions of maximum variation in the data. Despite the numerous sources of experimental variability that can account for the general disagreement in results generated from different microarray experiments using comparable samples, reduction of experimental bias to facilitate the integration of multiple datasets and a successful meta-analysis is feasible. For each dataset, the normalized base-two log transformed expression values for each significant differentially expressed gene in all samples were extracted and assimilated into a single dataset.

Prior to the assembly of this dataset, missing values in the individual datasets, allowed by our gene filtering pre-processing step, were replaced with estimated values using local least squares imputation (LLSimpute) implemented through the nni function of the Bioconductor package pcaMethods. Genes with no expression values in one or more datasets were removed. The resulting dataset was transposed so that genes are in columns (variables) and expression data for each gene are mean-centered and scaled to unit variance. PCA was then performed with the prcomp function provided by the R stats package.

Data analysis was performed primarily through the use of R packages (http://www.R-project.org) available through the open source software project Bioconductor (http://www.bioconductor.org). Further evaluation of the final biomarker panel was accomplished through assessment of the published data linking genes to PDAC as well as laboratory exploration of S100P and TMPRSS4 in PDAC cell lines and human tissue.

Antibodies and Reagents

Dulbecco's Modified Eagle's Medium (DMEM), phosphate-buffered saline (PBS), fetal bovine serum (FBS), trypsin ethyelediamine tetraacetic acid (EDTA), glutamine, penicillin streptomycin, and culture supplements were purchased from Gibco-BRL Life Technologies (Palto Alto, Calif., US). Propidium Iodide (PI) was purchased from Sigma-Aldrich, Inc., (St. Louis, Mo., US). S100P and TMPRSS4 antibodies used in Western blots were purchased from Sigma (MO, US). All other reagents and materials were purchased from Thermo Fisher Scientific (GA, US).

Cell Line Cultures

Capanc-1, BXPC3, MIAPACA, Panc-1, ASPC1, PL45 cells were purchased from American Type Culture Collection (Rockville, Md., US) and HPDE cells, an immortalized pancreatic epithelial cell line, were obtained. These cells were maintained in Dulbecco's modification of Eagle's medium (DMEM) containing 10% fetal bovine serum, 1% penicillin/streptomycin, and 1% glutamine. Cell lines were cultured in BD Primaria tissue culture dishes, with dimensions of 100×20 mm at 37° C. with 5% $CO_2$ in a humidifier incubator and carried at $2.0×10^6$ cells/ml, passaging two to three times weekly as needed. Cells were pelleted by centrifugation at 2,500 rpm for 8 min at 4° C. and resuspended in fresh complete media in tissue culture plates 24 hrs before use in experiments to avoid any confounding gene expression that might occur because of handling. Confluent cells were harvested by trypsinization with 0.05% trypsin and 0.02% EDTA, pelleted by centrifugation at 2,500 rpm for 8 min at 4° C., and resuspended in fresh complete DMEM media and plated in BD Primaria tissue culture dishes 24 hrs before use in experiments.

Lentiviral Production and Infection

Lentiviral shRNAs targeting S100P (shS100P) and TMPRSS4 (shTMPRSS4) were obtained from Harvard Medical School (Boston, Mass.). The lentivirus was packaged by co-transfection of 293T cells with the shRNA expression vector, VSV-G (vesicular stomatitis virus-glycoprotein), and delta-VPR plasmids at the ratio of 1:0.9:0.1, using lipofectamine 2000 (Invitrogen, USA). Forty-eight hours after transfection, the supernatants containing lentiviral particles were harvested and titering was done using Hela cells.

S100P and TMPRSS4 infections

Capanc-1 and BxPC3 cells were plated in 10 cm dishes until 80% confluence. The day of infection, media was removed and replaced with 8 ml of complete media supplemented with polybrene (8 ug/ml) into each plate. 250 ul of virus was added to each plate and incubated for 24 hours. Cells were left to recover from infection for 24 hours before initiating selection with puromycin 3 ug/ml for three days.

Proliferation Assay

Cell viability was indirectly assessed with a colorimetric, (3-(4, 5-dimethylthiazol-2-yl)-5-(3-carboxymethoxyphenyl)-2-(4-sulfophenyl)-2H-tetrazolium) (MTS) assay obtained from Promega. In brief, $5×10^3$ cells/well (100 µl/well) were plated on Fisher brand 96 well cluster dishes and infected with shS100P and shTMPRSS4. After 24 hours of incubation, DMEM medium was removed and followed by the addition of 20 µl of MTS solution to each well. The 96 well plates were placed in an incubator at 37° C. in 5% $CO_2$.

The absorbance of the solution was measured in a spectrophotometer (Bio-Rad Model 550, Bio-Rad Laboratories, Inc., Hercules, Calif., USA) using a test wavelength of 540 nm.

Example 1

Identification of Biomarkers

A search of the literature and publicly available microarray repositories identified four training datasets with evaluation of normal pancreas tissue and PDAC samples (Table 1). In addition, five validation datasets from public databases or literature were identified for testing the performance of the optimized biomarker panel on independent datasets and four additional datasets were collected for prospective validation (Table 1). All datasets utilized oligonucleotide-based microarray platforms, with eight studies using one of three versions of Affymetrix GeneChip arrays, and one study using Agilent-based microarrays. The independent validation datasets evaluated i) PDAC versus normal, ii) PDAC versus other tumors (e.g. breast, colon, liver, lung, and prostate), iii) PDAC versus chronic pancreatitis, and iv) normal versus pre-malignant pancreas lesion (intraductal papillary-mucinous neoplasm ([IPMN]) versus invasive cancer originating in intraductal papillary mucinous neoplasm (IPMN) (Table 1).

TABLE 1

Datasets used for development and validation of PDAC specific potential biomarker

| Dataset | Normal | Tumor | Sample Type | Platform |
|---------|--------|-------|-------------|----------|
| A) Training sets: | | | | |
| Set1 | 6 | 6 | Microdissected | U133A |
| Set2 | 9 | 13 | " | " |
| Set3 | 35 | 35 | Whole Tissue | Plus 2.0 |
| Set4 | 14 | 36 | " | " |
| B) Independent validation sets: | | | | |
| V1 | 7 | 25 | Whole Tissue | Plus 2.0 |
| V2 | 45 | 45 | " | Gene St 1.0 |
| V3 | 0 | 36 | Whole Tissue | Plus 2.0 |
| V4 | 0 | 18 | " | " |
| V5 | 145 | 0 | Tissues | U133A |
| C) Prospective validation sets: | | | | |

| Dataset | Group1 | Pan Tumor | Sample Type | Platform |
|---------|--------|-----------|-------------|----------|
| P1 | 6 (Normal) | 15 (IPMA + IPMC + IPMN) | Whole Tissue | U133A |
| P2 | 9 (Pancreatitis) | 6 | " | U133A |
| C1 | 4 (Normal) | 28 | Whole Tissue | Agilent |
| M1 | 25 (other Cancers) | 11 | Tissues | U133A |

Figure 2:
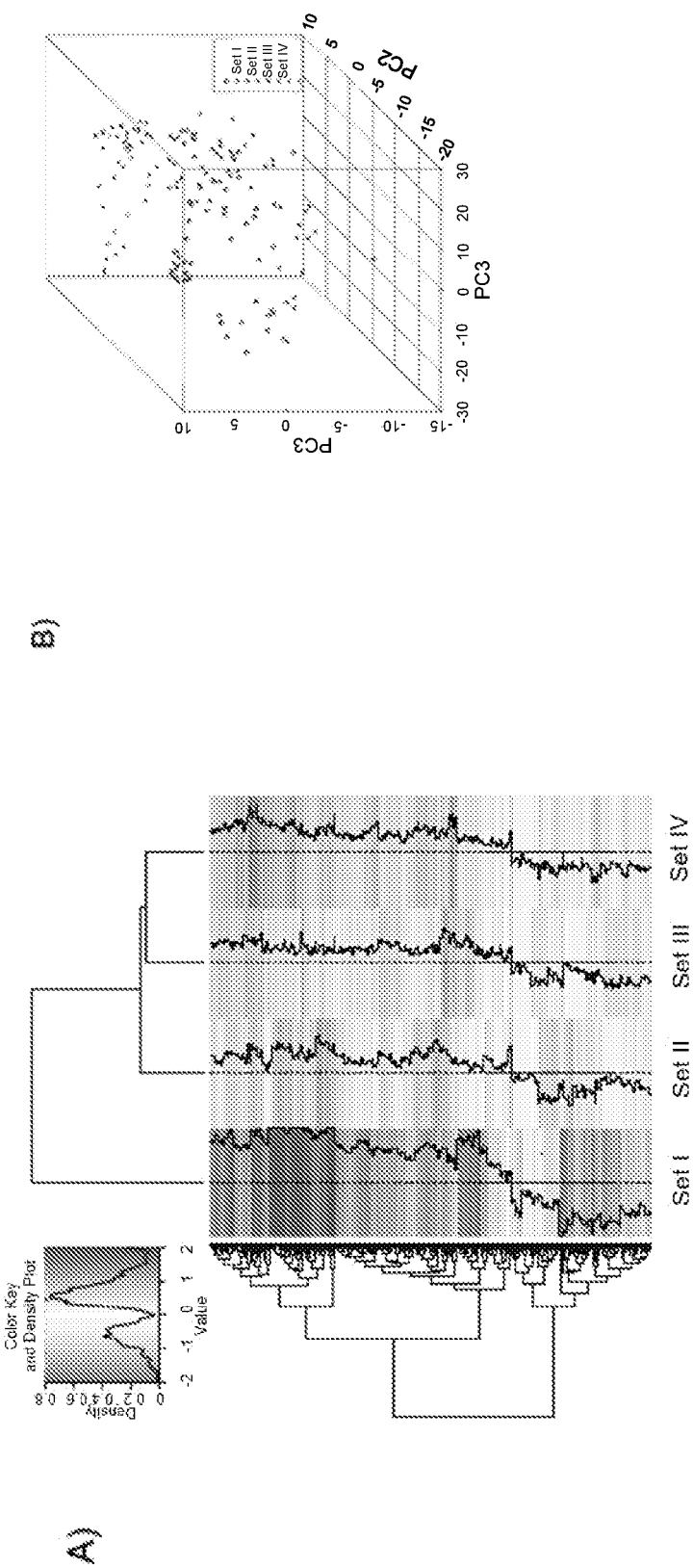
FIG. 2 is an image that illustrates the meta-signature of genes that are consistently differentially expressed in multiple set datasets. A) Signal to Noise ratio based heatmap of meta-signature genes B) PCA plot using meta-signature genes. PCA for 371 genes found to be differentially expressed in the same direction in four datasets. Differentially expressed genes are defined by an associated limma p-value less than 0.05 with Benjamini and Hochberg method for multiple comparison correction to control FDR.

The comparative reanalysis of raw expression data from four independent PDAC transcriptional profiling data sets with the empirical Bayes approach and using identical normalization and statistical methods for each data sets resulted in four lists of differentially expressed genes. In total, 11,322 significantly differentially expressed genes were identified in the four training datasets. Heatmaps for the top up- and down-regulated genes in two datasets are shown in FIG. 1A. Venn diagram analysis of the differentially expressed genes of the four datasets identified 409 genes common with concordant directionality to at least two of the four datasets (FIG. 1B). FIG. 2A shows a heatmap of the relative ratio of gene expression in PDAC compared to normal pancreas for each of the concordant genes across the four datasets, with the extent of overexpression or underexpression denoted by red or blue shading, respectively. The final combined ranked list of differentially expressed genes included 371 genes.

PCA analysis using the expression profiles of genes found to be significantly differentially expressed suggest the dominant patterns of gene expression are mostly associated with variation between the two sample classes (NP and PDAC) (FIG. 2B). While samples of the same class from the same independent study tend to group together, PDAC samples across all datasets, for the most part, are clearly separated from normal pancreas samples. The general clustering of the samples by class indicates that the biological variation of the samples overshadows any variations resulting from biases of the independent studies (FIG. 2B).

Example 2

Class Prediction Analysis in the Four Training Sets

Figure 3:
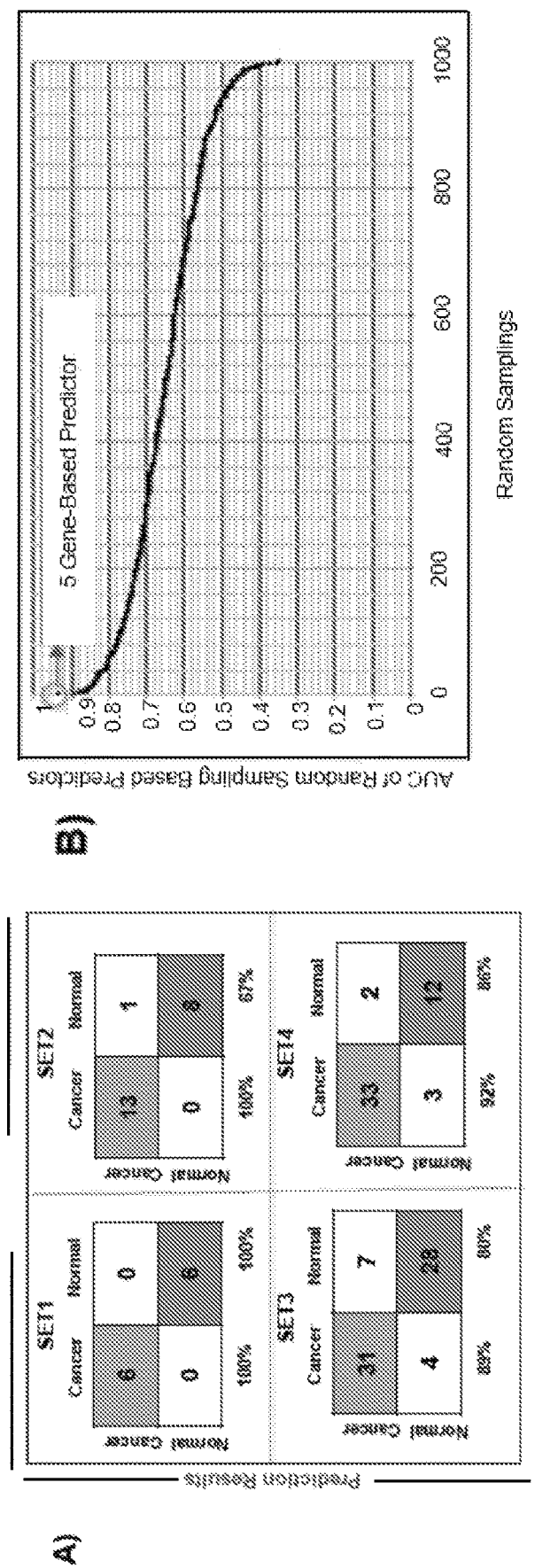
FIG. 3 is an image that illustrates the performance of a 5 gene based biomarker panel on training sets determined using leave one out cross-validation (LOOCV) 6 0.
Figure 4:
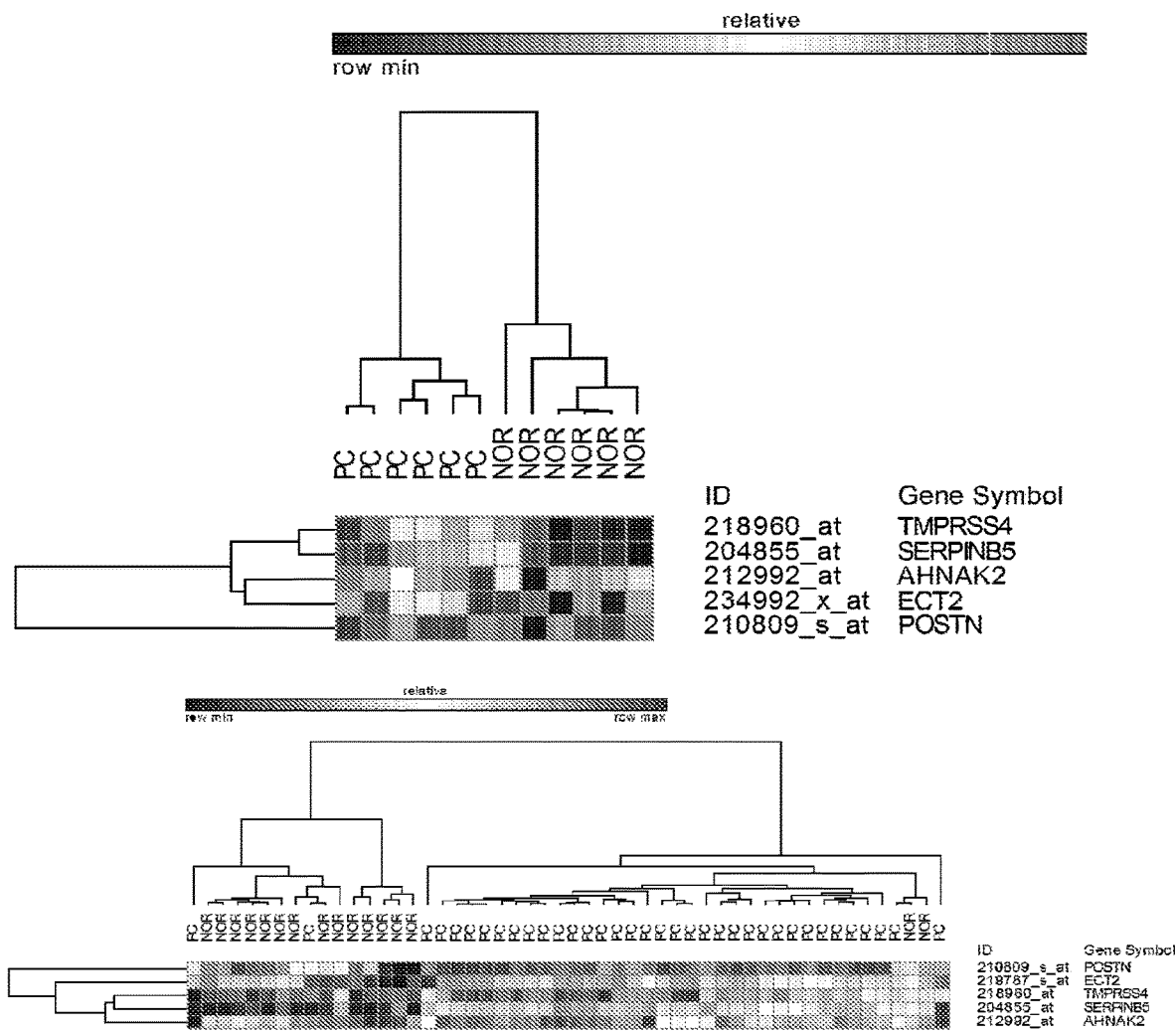
FIG. 4 is an image that illustrates hierarchical clustering of representative genes in PDAC and normal samples.

Class prediction analysis generated a large number of PDAC classifiers containing two to 40 genes each. Based on LOOCV evaluation in the training sets, classifiers containing five or ten genes performed with highest accuracy. The gene list for the 5- and 10-gene classifiers in the training sets is shown in Table 2. LOOCV of the 5-gene predictor with each of the four training datasets demonstrated good performance for each dataset individually with sensitivity ranging from 0.89-1.0 and specificity from 0.67-1.00 (FIG. 3A) resulting in a median area under the ROC curve (AUC) of 0.93 (FIG. 3B). The AUC plot in FIG. 3C depicts the threshold independent performance of this predictor. Hierarchical clustering of either the 5-gene or 10-gene classifiers (FIG. 4) demonstrates the relative differential expression of these genes in the four training sets and clearly shows that both classifiers separate the microdissected as well whole tissue PDAC samples from the normal controls with high sensitivity and specificity, although in most data sets the 5-gene classifier appears to separate more accurately.

Figure 5:
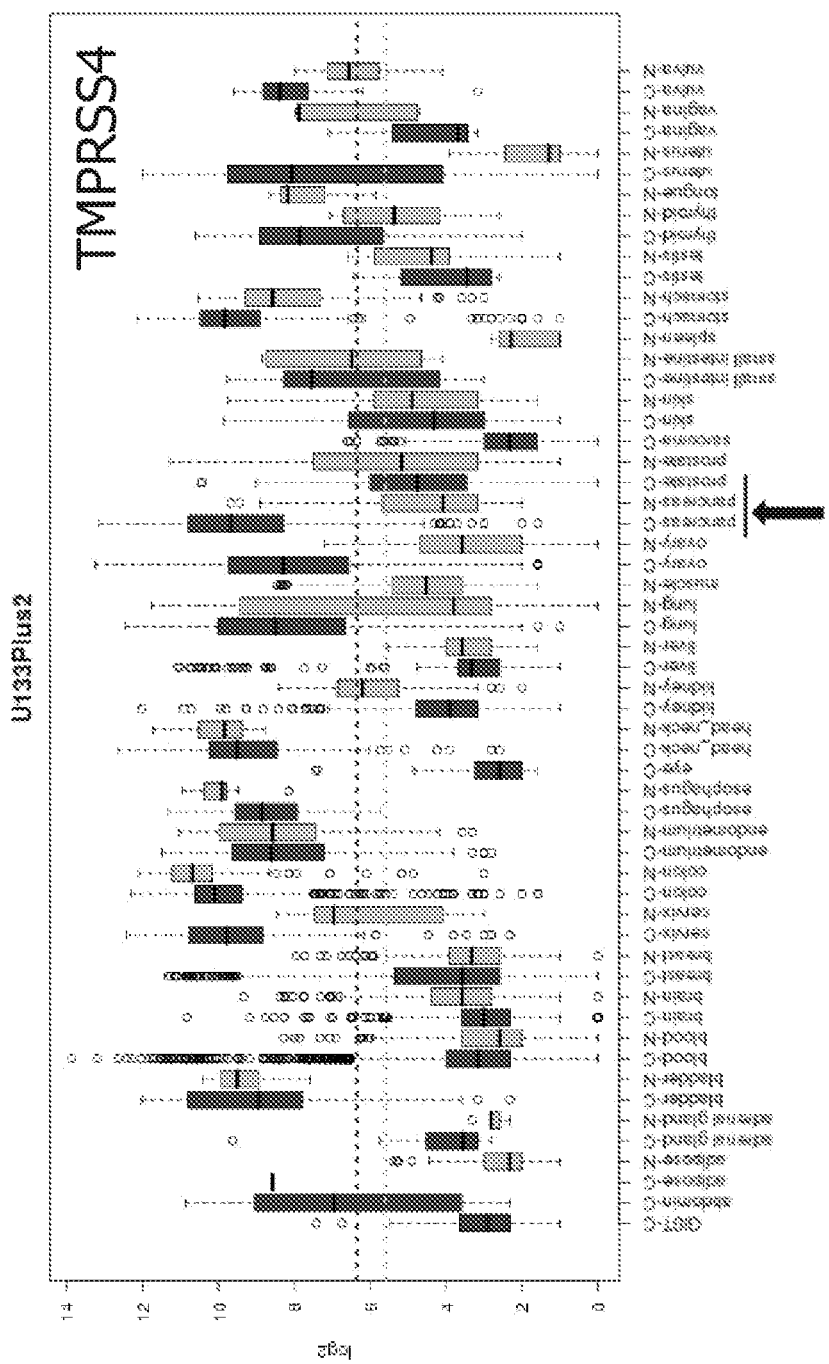
FIG. 5 is a graph depicting GENT database expression of a 5 gene panel in PDAC and other cancers.
Figure 5:
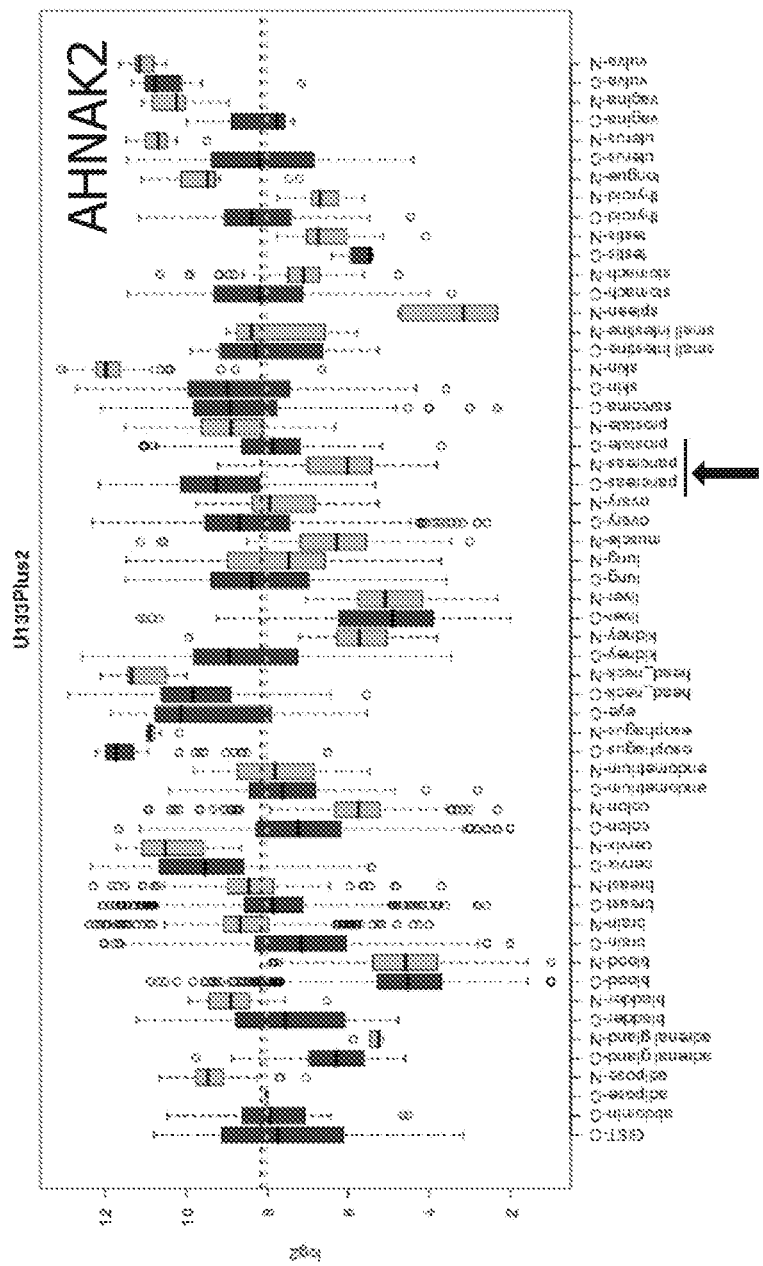
Figure 5:
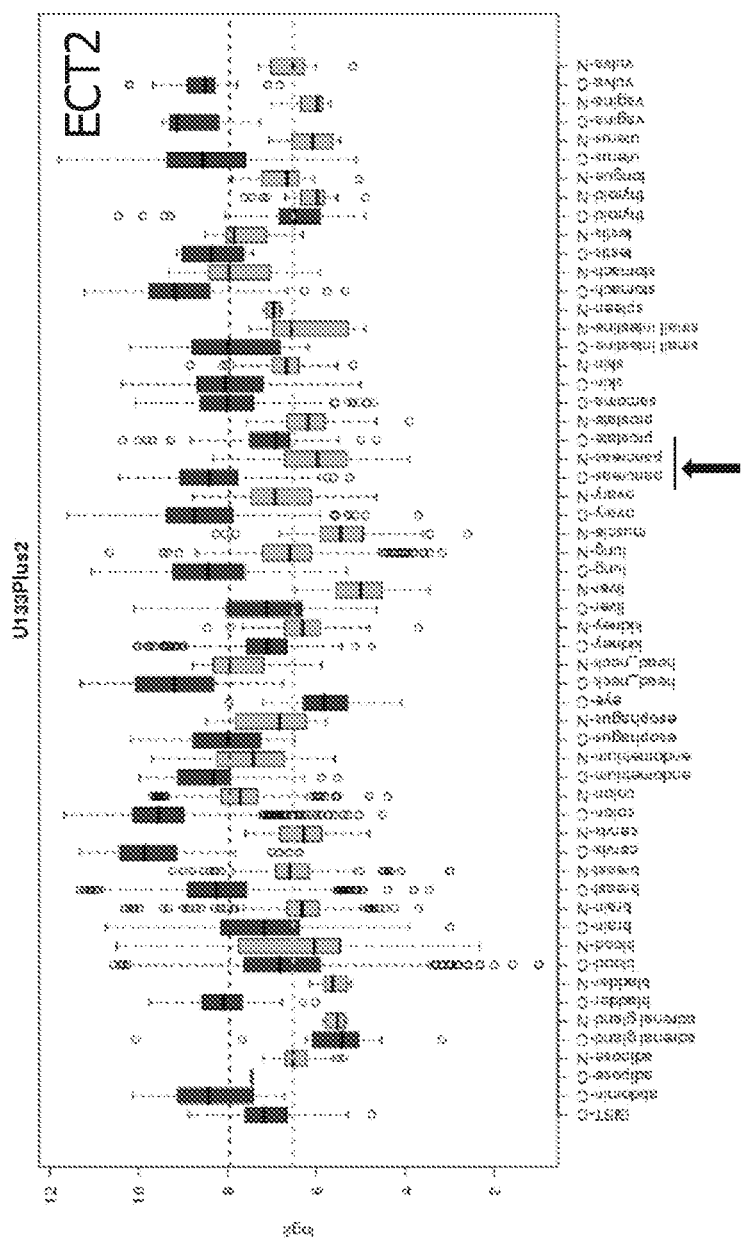
Figure 5:
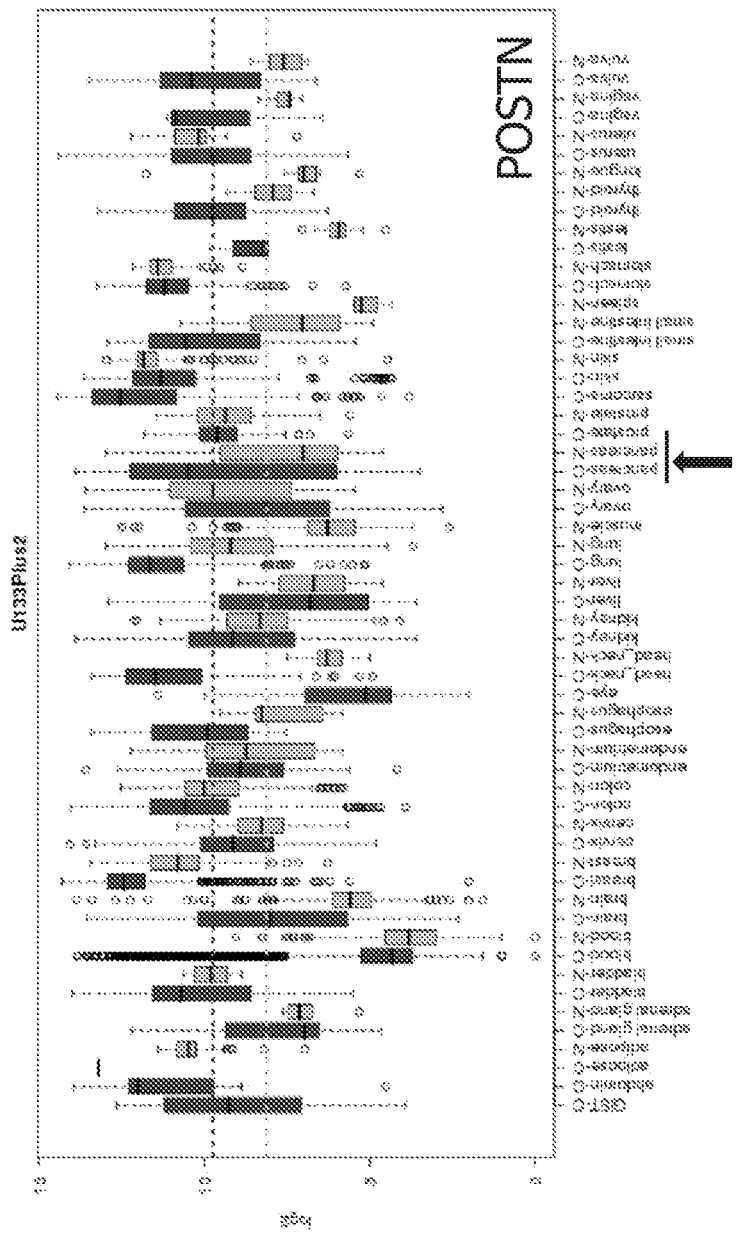
Figure 5:
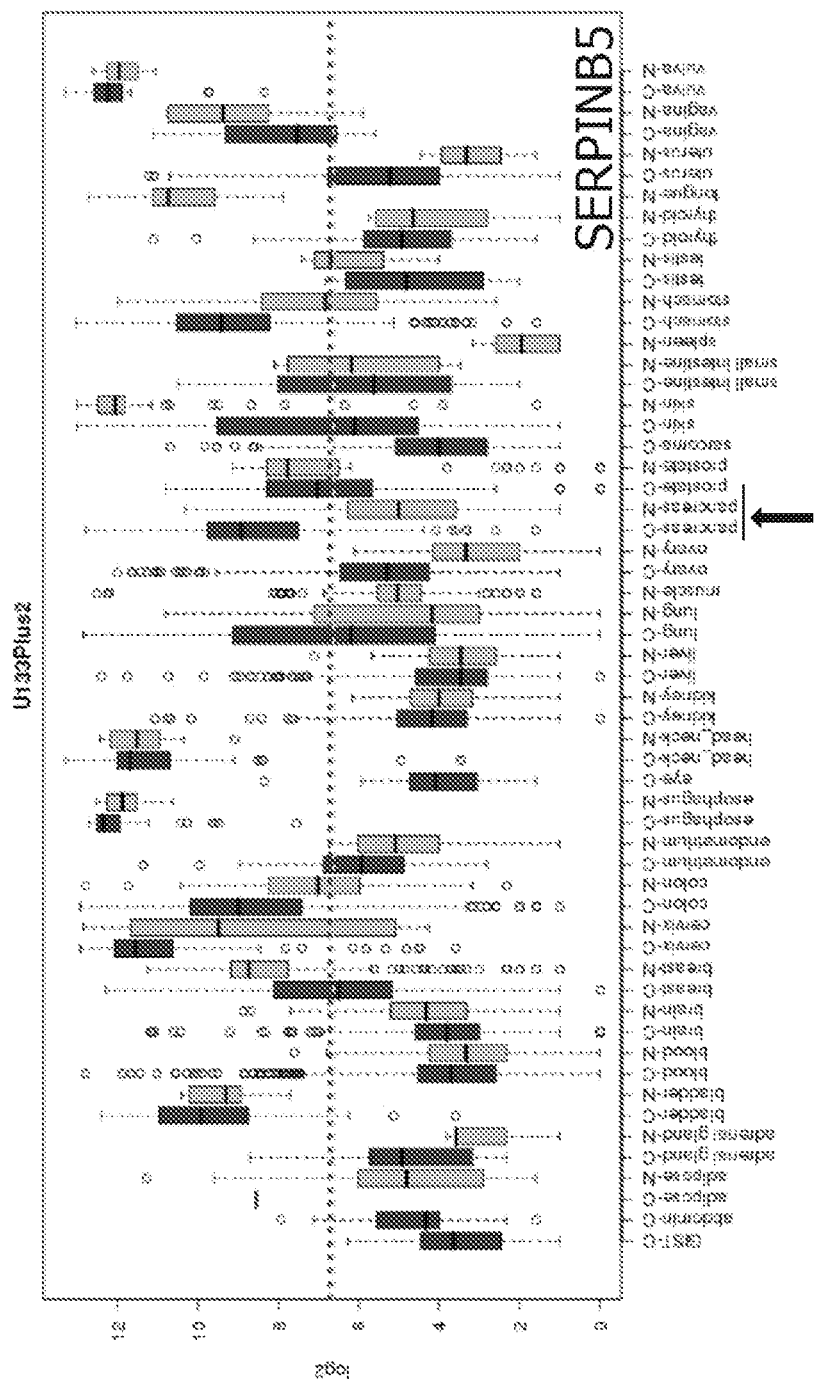

Evaluation of the GENT database that compares relative expression of genes between different cancers and their normal tissue counterparts indicates that indeed all 5 genes in the 5-gene classifier are overexpressed in PDAC compared to normal pancreas (FIG. 5). Moreover, this analysis suggests that TMPRSS4 is also overexpressed in cervical, ovarian, stomach, thyroid, and vulval cancer, SERPIN B5 is overexpressed in cervical, colon, ovarian, and stomach cancer, POSTN is overexpressed in brain, breast, esophageal, head and neck, lung, small intestine, thyroid, vaginal, vulval and testicular cancer, ECT2 is overexpressed in many types of cancer, and AHNAK2 is overexpressed in colon, kidney, stomach, and thyroid cancer.

dicted the class of PDAC samples, corresponding to a sensitivity of 96% and 88.89% and a specificity of 85.7% and 86.67%, respectively in two independent validation sets that contained PDAC and normal pancreas samples, which is significantly better than CA19-9, and exhibited a specificity of 85.7% and 86.67% respectively. The AUC for these two datasets reached 0.9 and 0.8778. In two datasets containing exclusively PDAC samples a sensitivity of 97.22% and 94.5% was achieved and in a dataset containing 145 normal samples a specificity of 96.5% was determined.

Figure 6:
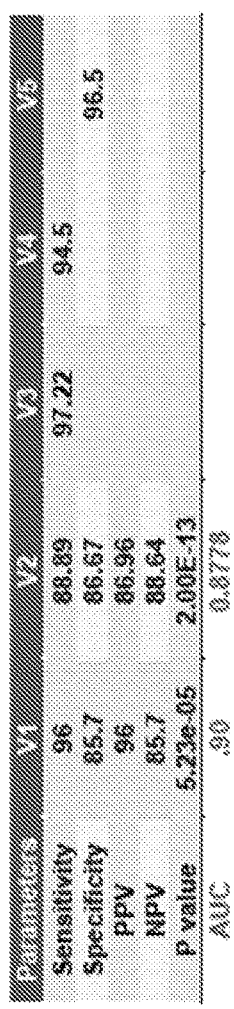
FIG. 6 is an image that illustrates performance of 5 genes based Biomarkers on independent validation and prospective sets. A) Performance on independent validation sets, B) Pancreatitis vs. Pancreatic Cancer and C) Normal pancreatic duct compared to intraductal papillary-mucinous adenoma (IPMA), intraductal papillarymucinous carcinoma (IPMC) and intraductal papillary mucinous neoplasm (IPMN) samples.
Figure 6:
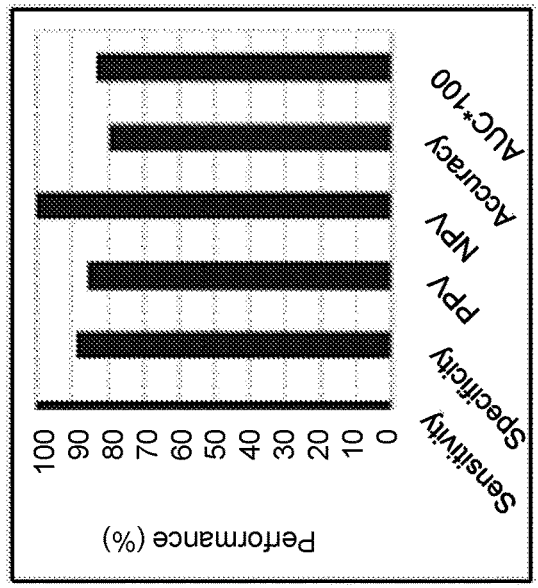

To further determine whether the classifier can distinguish between PDAC and benign pancreatic disorders, we tested the 5-gene classifier on a prospective dataset that includes 6 PDAC samples and 9 chronic pancreatitis samples. Specificity was 88.9% and sensitivity 100% with an overall accuracy of 93.3% and AUC of 0.94 (FIG. 6B). Thus, the predictor is able to also distinguish between PDAC and other non-malignant pancreatic diseases.

We further validated this 5-gene predictor in a dataset containing normal pancreatic duct, intraductal papillary-mucinous adenoma (IPMA), intraductal papillary-mucinous carcinoma (IPMC), intraductal papillary-mucinous neoplasm (IPMN). The 5-gene predictor separated IPMA, IPMC, and IPMN from normal pancreatic duct with 100% sensitivity and 83.3% specificity, achieving an AUC of >0.9 (FIG. 6C).

Figure 7:
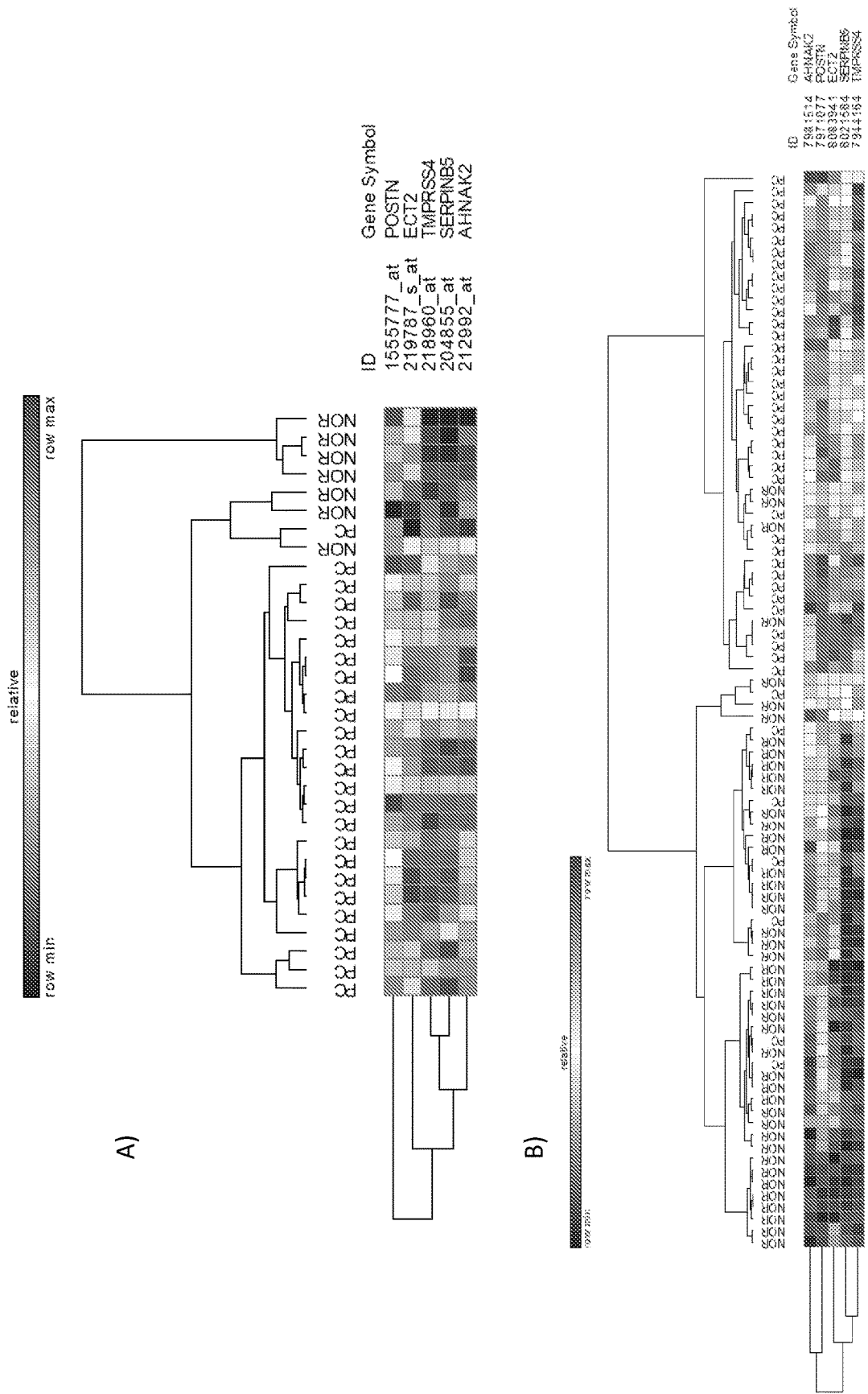
FIG. 7 is an image that illustrates hierarchical clustering of representative genes in PDAC and normal samples.

Cross-platform evaluation also demonstrated that the predictor was able to achieve a sensitivity and specificity of 0.96 and 0.75 respectively and an AUC of 0.84 in a dataset of pancreatic cancer versus normal pancreas generated using the Agilent platform (FIG. 7A). Further evaluation on an additional independent dataset that included 11 PDAC samples and 25 tumor samples of various origins (breast, colon, liver, lung, prostate) resulted in sensitivity of 96.4% and specificity of 75% (FIG. 7B).

TABLE 2

List of genes from 5- and 10-gene PDAC classifier

| 10 Gene | 5 Gene | Gene Symbol | Gene ID | Description | Sub-Cellular Localization | Differentially Expressed |
|---|---|---|---|---|---|---|
| 10 Gene based Biomarker | 5 Gene Based Biomarker | ECT2 | 1894 | Epithelial cell transforming sequence 2 oncogene | Nucleus | ↑↑↑↑ |
| | | AHNAK2 | 113146 | AHNAK nucleoprotein 2 | unknown | ↑↑↑ |
| | | SERPINB5 | 5268 | Serpin peptidase inhibitor, clade B (ovalbumin), member 5 | Extracellular Space | ↑↑↑ |
| | | TMPRSS4 | 56649 | Transmembrane protease, serine 4 | Plasma Membrane | ↑↑↑ |
| | | POSTN | 10631 | Periostin, osteoblast specific factor | Extracellular Space | ↑↑↑ |
| | | S100P | 6286 | S100 calcium binding protein P | Cytoplasm | ↑↑↑ |
| | | CEACAM5 | 1048 | Carcinoembryonic antigen-related cell adhesion molecule 5 | Plasma Membrane | ↑↑↑ |
| | | GABRP | 2568 | Gamma-aminobutyric acid (GABA) A receptor, pI | Plasma Membrane | ↑↑↑ |
| | | CELA2B | 51032 | Chymotrypsin-like elastase family, member 2B | Extracellular Space | ↓↓↓ |
| | | CUZD1 | 50624 | CUB and zona pellucida-like domains 1 | Plasma Membrane | ↓↓↓ |

Example 3

Figure 8:
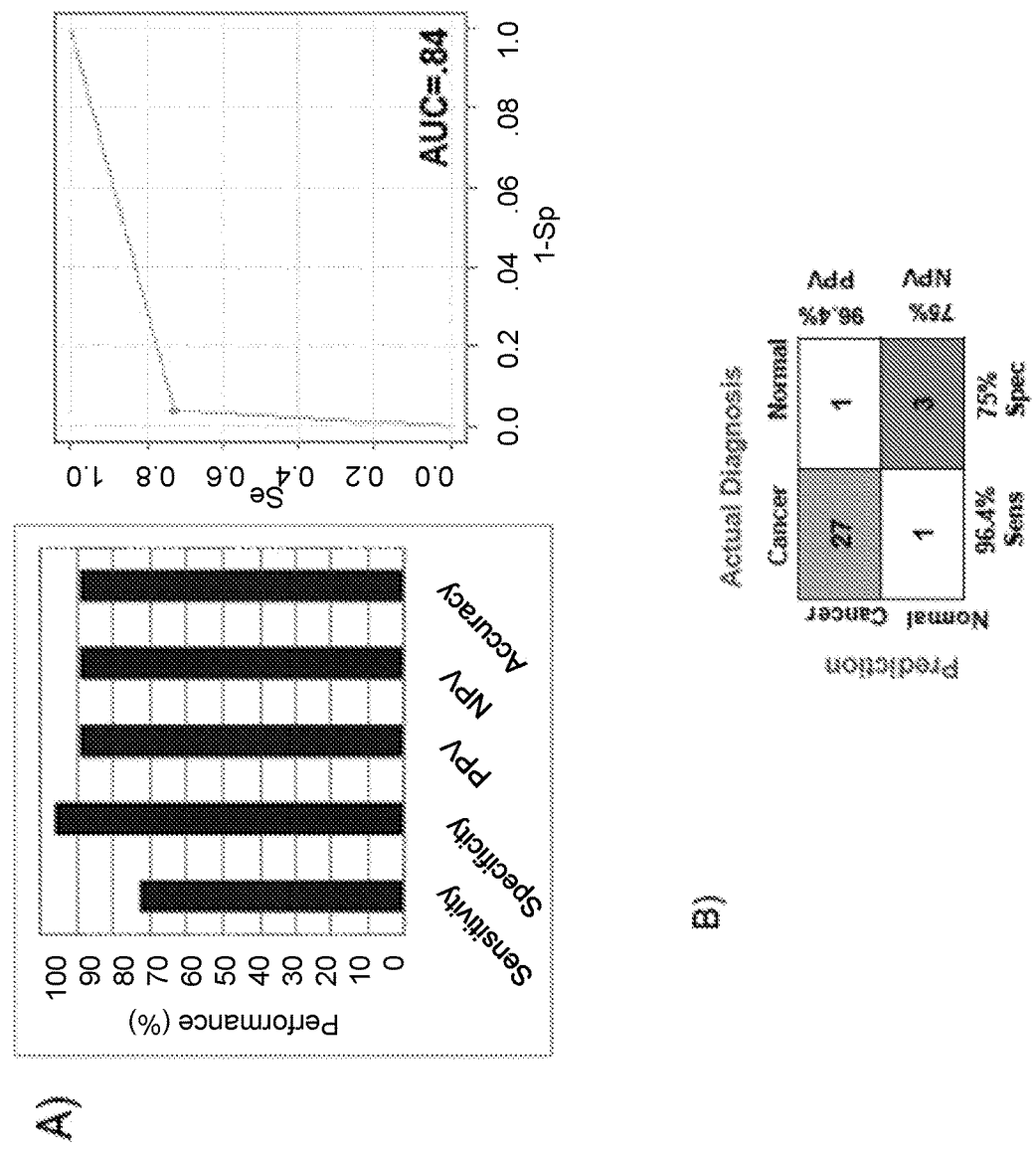
FIG. 8 is an image that illustrates PDAC specificity and cross-platform stability analysis. A) Classification of pancreatic cancer vs. Other Cancers (Breast, Colon, Lung), and B) Normal vs. pancreatic cancer analysis on a dataset from Agilent platform.

The 5-Gene PDAC Classifier Predicts PDAC with High Accuracy in 9 Independent Validation Sets The 5-gene based classifier had the highest accuracy in the independent test sets when compared to biomarkers containing 10 genes (FIG. 6A). This classifier consists of 5 upregulated genes. The 5-gene classifier accurately pre- To determine the expression levels of the 5-gene classifier across the various samples in the different validation sets we generated heatmaps after hierarchical clustering of each data set utilizing the 5 genes. Hierarchical clustering of validation sets 1 (7 normal vs. 25 PDAC) and 2 (45 normal vs. 45 PDAC) establishes that the 5-gene PDAC classifier accurately separates normal from PDAC samples and that expression of the 5 genes clearly indicates that the 5 genes for the most part are overexpressed in PDAC as compared to normal pancreas (FIG. 8A). Hierarchical clustering of validation set 1 separates all normal from PDAC and only one of 25 PDAC sample clusters with the normal samples, whereas in validation set 2 7 of 45 PDAC samples cluster with the normal samples and 4 of 45 normal samples with the PDAC samples (FIG. 8A). The classifier performs well whether the Affymetrix U133 Plus 2.0 or Gene 1.0 ST GeneChip is used, even though these two array types use different probe sets, further highlighting the robustness of the classifier. FIG. 8B demonstrates that the 5-gene classifier indeed separates all early PDAC precursor IPMN, IPMA and IPMC samples from the normal pancreas samples except one normal sample that clusters with the early PDAC precursors. Interestingly, one of the 5 genes, POSTN, did not appear to separate the early precursors well, but did not significantly affect the overall performance of the 5-gene PDAC predictor. TMPRSS4 and SERPINB5 appeared to provide the strongest discrimination with regard to early precursors. Furthermore, the 10-gene predictor performed somewhat better for this particular data set, since all normal samples separated accurately from all early stage PDAC samples.

Example 4

Real Time PCR Validation of PDAC Biomarkers

Figure 9:
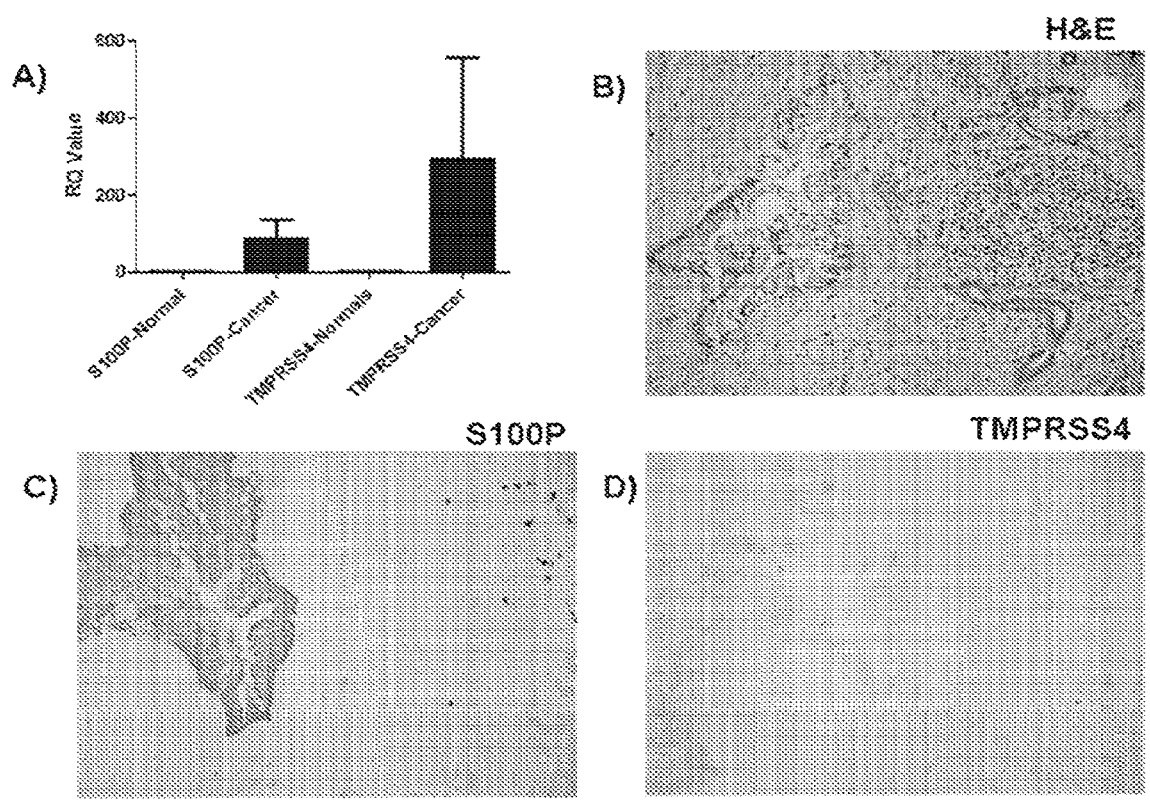
FIG. 9 is an image that illustrates validation of S100P and TMPRSS4 genes expression by using QRT-PCR (A) from 9 paired pancreatic cancer and normal samples, and Immunohistochemistry (B, C, D) from 19 cases of PDAC. A) QRT-PCR based validation of S100P and TMPRSS4 genes expression using 9 paired pancreatic cancer and normal samples. The PDAC samples were paired with non-tumor pancreatic tissue from the same patients; B) Hematoxylin and eosin-stained image of a single neoplastic gland of PDAC lying adjacent to smaller, scattered ducts of adjacent changes of chronic pancreatitis (200× magnification); C) Diffuse, strong immunohistochemical expression of S100P is shown in a neoplastic duct with negativity in adjacent reactive ducts (200× magnification); D) Moderate, but diffuse cytoplasmic expression of TMPRSS4 is demonstrated in the large neoplastic duct with weak staining demonstrated in adjacent reactive ductal epithelium.

We have validated the expression pattern of S100P and TMPRSS4 candidates using 9 paired pancreatic cancer and normal samples by real time PCR analysis (FIG. 9A). The PDAC samples were paired with non-tumor pancreatic tissue from the same patients. The results clearly demonstrate that the expression of the S100P and TMPRSS4 biomarkers are detected mostly in PDAC samples, while normal samples do not seem to have significant expression.

Example 5

Immunohistochemical Validation of S100P and TMPRSS4 in PDAC Tissue Sections

Eight of the ten genes in the 10-gene PDAC classifier are overexpressed and two are underexpressed in PDAC. Table 2 lists these ten genes and a summary of their biological functions. Several of the 10 genes in the classifier have previously published data linking them to cancer-related functions including some of them in relation to PDAC, thus, suggesting that a subset of these ten genes may be valuable therapeutic targets for PDAC as well. Two of the overexpressed genes, S100P and TMPRSS4, were selected for further evaluation due to their strong apparent relevance for cancer and their potential "druggability" as secreted and transmembrane proteins, respectively. S100P, a 95-amino acid member of the S100 family of calcium binding proteins, and TMPRSS4, a protease of the Type II transmembrane serine protease (TTSP) family, have previously been demonstrated to be overexpressed in PDAC and several other cancers.

In order to further investigate potential differences in expression of S100P and TMPRSS4 in PDAC versus non-neoplastic tissue, whole tissue sections from 19 cases of PDAC (18 pancreatic resections and 1 liver metastasis) were studied. Unstained slides were stained as mentioned in the Materials and Methods section.

Importantly, S100P was found to be diffusely and strongly expressed in neoplastic ducts and glands of 19 of 19 PDAC cases (strong cytoplasmic and focal nuclear expression), but was not expressed in any non-neoplastic ducts within the same tissue sections, including those in adjacent areas of chronic pancreatitis. Moreover, S100P was found to be diffusely positive in 5 cases with extensive adjacent pancreatic intraepithelial neoplasia (PanIN), suggesting that S100P could be a marker expressed early in pancreatic ductal neoplasia (FIG. 9C). These results confirm and extend on those of previous publications. Background cytoplasmic staining was identified in neural elements including nerves and ganglia present within the tissue sections.

Similar to S100P, TMPRSS4 was diffusely expressed in the ducts/glands of PDAC, with 19 of 19 cases demonstrating cytoplasmic expression. Additionally, TMPRSS4 was expressed in all cases of Pancreatic Intraepithelial Neoplasia (PanIN), which suggests that TMPRSS4 may represent an early marker of pancreatic ductal neoplasia. However, non-neoplastic ducts also showed some expression in 8 of 19 cases (42%), though was typically seen at a level of lesser intensity than in neoplastic ducts (FIG. 9D). TMPRSS4 was also found to be expressed diffusely within the cytoplasm of acinar cells of the exocrine pancreas and within smooth muscle cells of large arteries and veins, often at an intensity equal to or greater than that of neoplastic pancreatic ducts. While TMPRSS4 overexpression in PDAC has previously been described, no published protein expression data are available.

Example 6 qRT-PCR Validation of the 5-Gene PDAC Classifier in Retrospective FFPE Patient Samples Demonstrates Overexpression of the 5 Genes in PDAC as Compared to Pancreatitis or Healthy Pancreas Method: Quantitative Real-Time PCR (qRT-PCR) Analysis of FFPE Samples Human formalin-fixed paraffin embedded (FFPE) tissue was obtained from 9 PDAC patients who underwent primary surgical resection (pancreaticoduodenectomy or partial pancreatectomy). The original slides (5 µm thickness) of FFPE tissue that were prepared and stained with hematoxylin and eosin were reviewed by a fellowship-trained gastrointestinal pathologist. Five well-differentiated and four moderately-differentiated PDAC samples and their respective background, non-neoplastic pancreatic parenchyma (four with no significant pathologic abnormality and five with pancreatitis) were selected. Regions of neoplastic and background pancreatic parenchyma were designated for analysis (areas at least 64 mm$^2$ in size were outlined with permanent marker).

After matching the tissue block with the H&E stained slide, core punches, restricted to the tumor regions that the pathologist marked as PDAC, pancreatitis or healthy pancreas, were extracted from the FFPE block. A 2.5 mm biopsy punch was used to punch three cores from each sample for RNA extraction. Total RNA was isolated using the Recov-erAll™ Total Nucleic Acid Isolation Kit (Ambion) after pooling the three cores for each sample.

Figure 10:
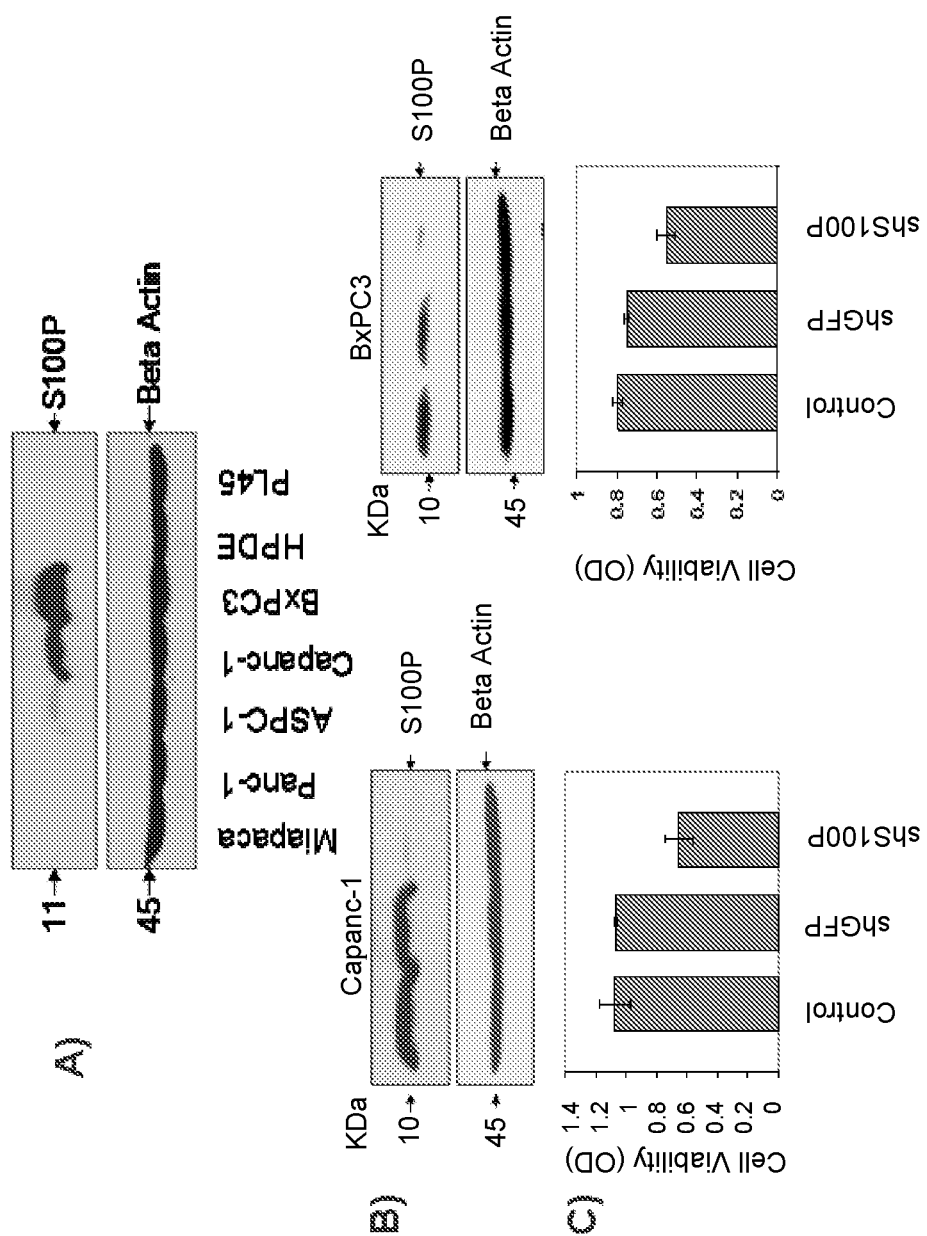
FIG. 10 is an image illustrating qRT-PCR validation of 5-gene PDAC classifier on retrospective microdissected FFPE samples from patients with PDAC. Total RNA was isolated from 9 matched pairs of PDAC and pancreatitis (n=5) or healthy pancreas (n=4). FFPE tissue blocks were inspected by the pathologist and marked regions of PDAC, pancreatitis and healthy pancreas microdissected. QRTPCR was performed on each sample for POSTN, SERPINB5, AHNAK2, TMPRSS4 and ECT2 in duplicates. Box plots of fold change (RQ values) of PDAC samples relative to their matched pancreatitis or normal pancreas samples after normalization to GAPDH are shown.

Results:

To determine whether the 5-gene PDAC classifier indeed discriminates PDAC from normal pancreas or benign pancreatic lesions, we developed a qRT-PCR assay for the classifier and evaluated the expression pattern of the 5-gene PDAC classifier in 9 microdissected paired retrospective FFPE patient samples containing pancreatic cancer and matched non-tumor normal pancreatic tissue (4 samples) or matched pancreatitis tissue (5 samples) (FIG. 10). Relative quantity (RQ) values were calculated by using the matched normal or pancreatitis tissue as the baseline to reflect the fold change in tumor samples. In all 9 matched pairs at least 4 of the 5 genes were elevated in pancreatic tumor tissues as compared to normal or pancreatitis tissue, and the box plots reflecting the relative expression of each gene compared to either matched normal or pancreatitis demonstrate clear discrimination, providing strong support that these 5 genes are selectively overexpressed in PDAC (FIG. 10). Most importantly, this differential expression of the 5 genes was validated in PDAC compared to pancreatitis, a clinically highly relevant differential diagnosis.

Example 7

The 5-Gene PDAC Classifier Distinguishes Between PDAC or Early Stage PDAC, PanIN, and Healthy Pancreas in the PDX1-Cre;LSL-Kras$^{G12D}$ GEM Mouse Model of PDAC While IPMNs have the potential to become malignant and progress towards PDAC, the majority of PDAC cases likely evolve from pancreatic intraepithelial neoplasia (PanIN) lesions containing Kras mutations. While PanINs are difficult to detect in humans, various genetically engineered (GEM) mutant Kras mouse models have been developed that spontaneously develop PDAC through the stages of PanIN development. One GEM PDAC model is the frequently used PDX1-Cre;LSL-Kras$^{G12D}$ model. These mice develop low and high-grade progressive ductal PanIN lesions with increasing age and a low frequency progression to invasive and metastatic PDAC upon activation of oncogenic Kras in the pancreas, phenocopying development of human PDAC. The 5-gene PDAC classifier was tested on an available Affymetrix microarray dataset of three biological replicates each of normal pancreatic tissue, PanIN and PDAC from the PDX1-Cre;LSL-Kras$^{G12D}$ mice. This gene expression dataset of PDAC, PanIN and healthy pancreas derived from the PDX1-Cre; LSL-Kras$^{G12D}$ GEM mouse model of PDAC (GSE33322) was available in the public databases.

Figure 11:
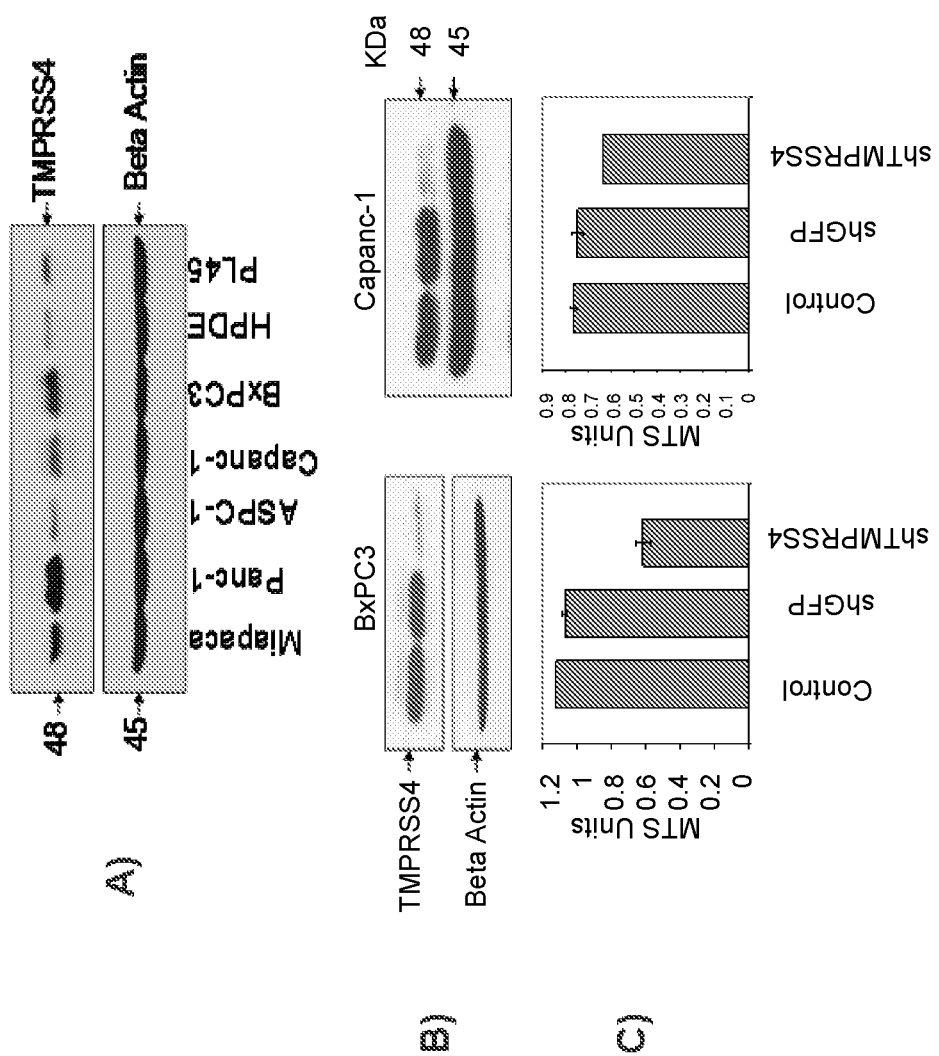
FIG. 11 is an image illustrating performance and expression of 5-gene PDAC classifier on independent mouse validation set. Cross-species performance of the 5-gene PDAC classifier on a GEM mouse model of PDAC. Hierarchical clustering of pancreatic tissue samples from three mice each for normal pancreas, PanIN and PDAC across the 5-gene PDAC panel.

Hierarchical clustering of this dataset using the equivalent mouse GeneIDs demonstrated that all 5 genes were upregulated in both PanINs and PDAC compared to normal pancreas, resulting in perfect separation of PanINs and PDAC samples from normal pancreas (FIG. 11). Interestingly, PanINs perfectly separated from PDAC. PanIN samples clustered on the same main branch as the normal pancreas, but on a separate subbranch within this tree, suggesting that PanIN is indeed a stage different from normal, but in between normal and PDAC. POSTN exhibited the same level of overexpression in PanIN and PDAC compared to normal pancreas, TMPRSS4 is higher expressed in PanIN than PDAC, and ECT2, AHNAK2, and SERPINB5 are higher expressed in PDAC (FIG. 11). These results provide the strongest evidence that the 5-gene PDAC classifier is able to discriminate early PDAC precursor lesions from normal pancreas and that differential expression of these 5 genes may even differentiate between PanIN and PDAC, suggesting dynamic, malignancy-related changes of these 5 genes during PDAC development.

Example 8

Figure 12:
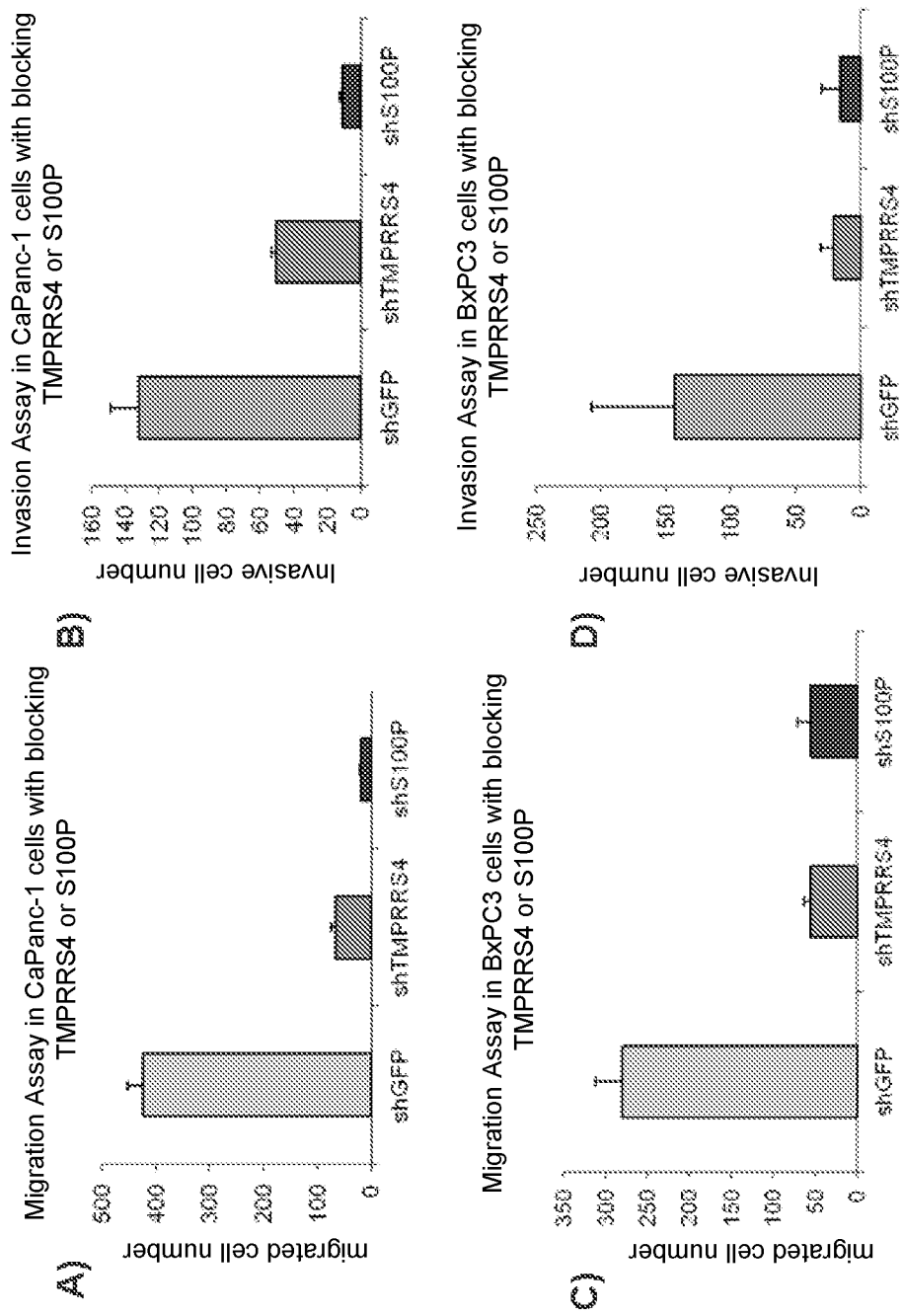
FIG. 12 is an image that illustrates verification of S100P protein expression in various PDAC cells (A). Western Blot analysis of S100P knockdown (B) seventy-two hours after shS100P infection protein lysate was generated and analyzed. Cell viability was also determined using MTS (C).
Figure 13:
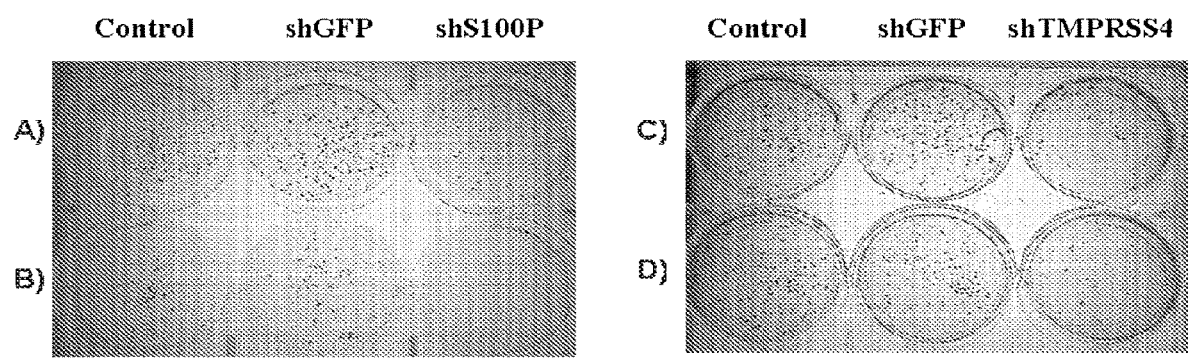
FIG. 13 is an image that illustrates verification of TMPRSS4 protein expression in various PDAC cells (A). Western Blot analysis of TMPRSS4 knockdown (B) seventy-two hours after the shTMPRSS4 infection protein lysate was generated and analyzed. Cell viability was also determined using MTS (C).

S100P or TMPRSS4 Knockdown Decrease PDAC Cell Migration, Invasion, and Anchorage-Independent Growth in Soft Agar While S100P protein expression in PDAC cell lines has previously been analyzed, TMPRSS4 protein expression has not previously been studied in detail. Increased protein expression of both S100P and TMPRSS4 in several different pancreatic cancer cell lines as compared to the immortalized pancreatic epithelial cell line, HPDE (FIGS. 12A and 13A) was verified by Western blot analysis. The functional relevance of S100P for PDAC cell invasion and migration has been established; however, the role of TMPRSS4 in PDAC cells has not been determined, even though TMPRSS4 has been demonstrated to induce invasion and epithelial-to-mesenchymal transition (EMT) of colorectal cancer cells. We generated lentiviral vectors expressing shRNAs against S100P (shS100P) and TMPRSS4 (shTMPRSS4) and infected PDAC cell lines (Capanc-1, BxPC-3) expressing high levels of S100P or TMPRSS4, respectively, with these lentiviruses or lentivirus expressing shGFP. ShS100P and shTMPRSS4 knocked down the expression of their respective target proteins by more than 80% in both cell lines without affecting β-actin expression (FIGS. 12B and 13B). Moreover, the knock-down of S100P and TMPRSS4 clearly decreased cell viability, as measured with MTS assay, in both Capanc-1 and BxPC3 cells (FIGS. 12C and 13C).

Figure 14:
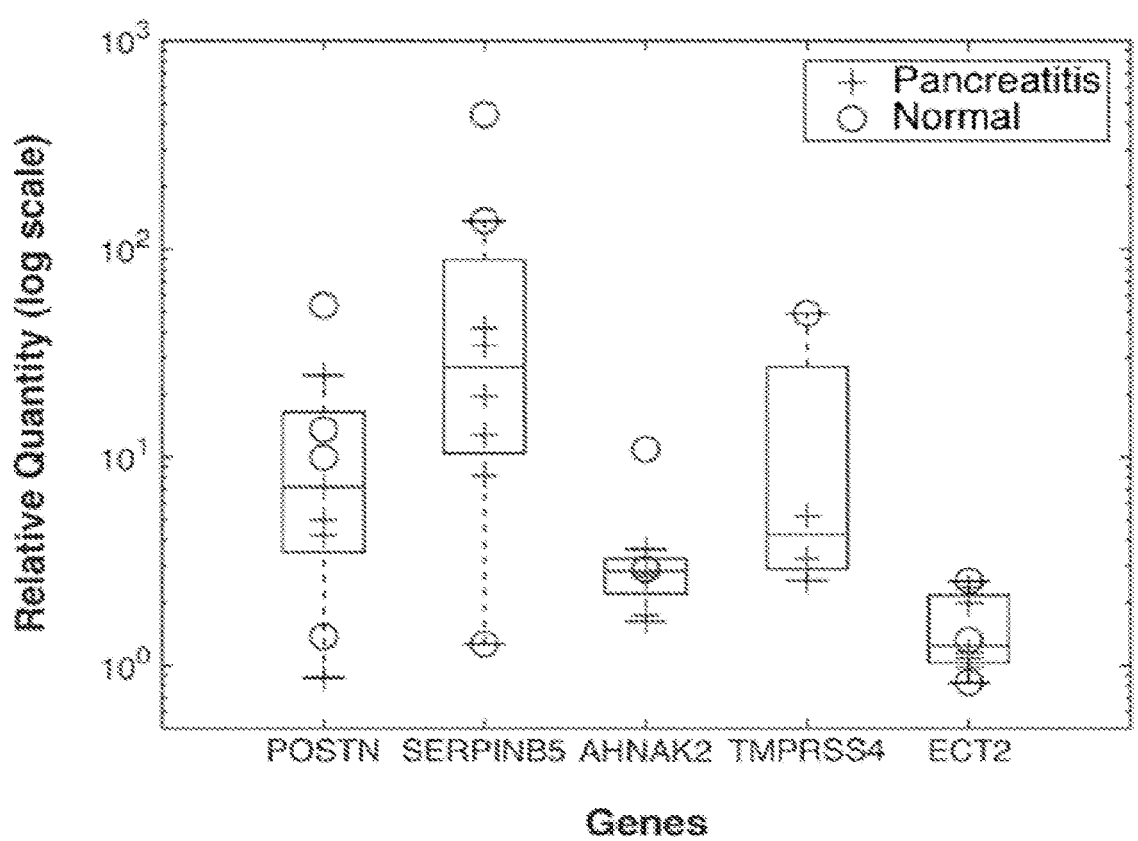
FIG. 14 is an image that illustrates S100P and TMPRSS4 knockdown reduces PDAC cell migration and invasion. A & C, quantification of cells migrating through fibronectin-coated membranes. B&D, quantification of cells invading through Matrigel-coated membranes after 16-h incubation and 10% serum as chemoattractant.

We next evaluated the effect of S100P or TMPRSS4 knockdown on serum-induced migration of PDAC cells, CaPanc-1, BxPC-3, in a Transwell chamber assay. In CaPanc-1 and BxPC-3 cells, shS100P and shTMPRSS4 decreased the ability of PDAC cells to migrate through the pores by 80-90% compared with shGFP-treated cells (FIGS. 14A and C). Because cell migration is a process that promotes tumor invasion, we tested the effect of S100P and TMPRSS4 knockdown on cell invasion using Matrigel-coated Transwell chambers. S100P or TMPRSS4 knockdown compared with shGFP strongly decreased CaPanc-1 and BxPC-3 invasion by 62-92% after 16-h incubation (FIGS. 14B and D). These results confirm the previous findings for S100P and demonstrate that TMPRSS4 is an inducer of PDAC cell migration and invasion as well.

Figure 15:
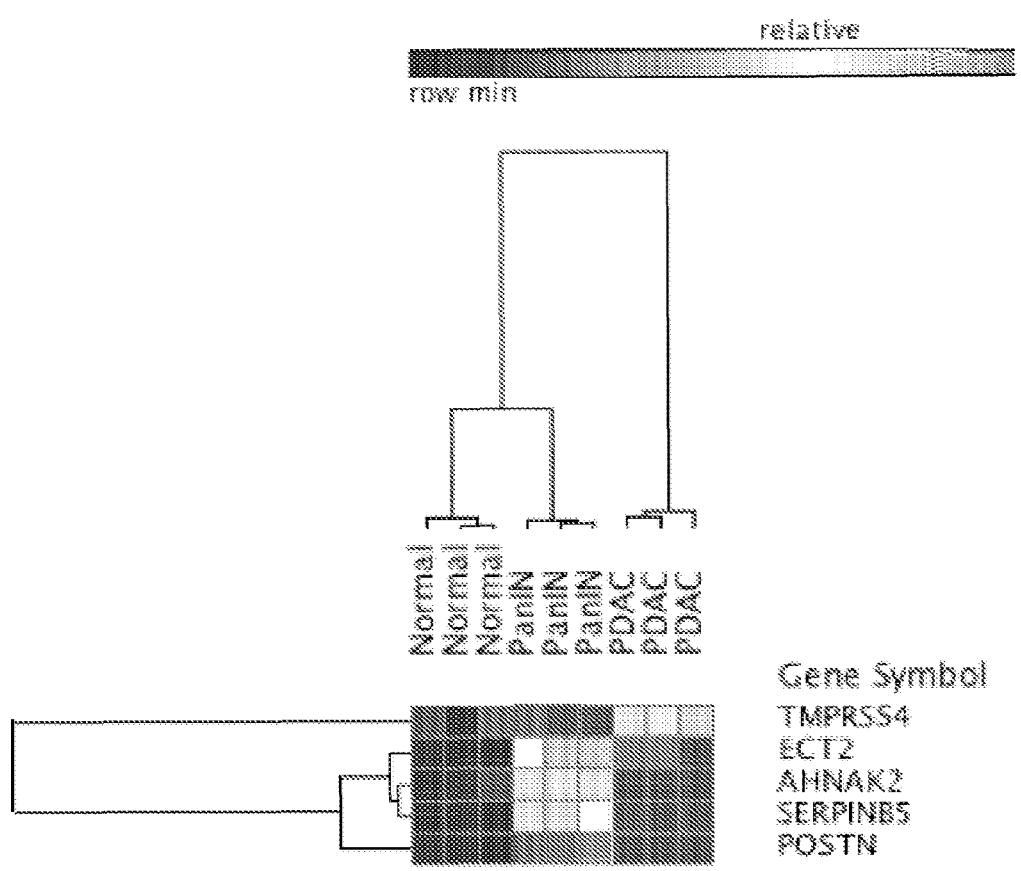
FIG. 15 is an image that illustrates S100P & TMPRSS4 knockdown reduces anchorage-independent growth in Capanc-1 and BxPC3 cells, in a soft agar assay.

Moreover, one of the hallmarks of oncogenic transformation is the loss of anchorage-dependent growth as demonstrated by the ability to form colonies in soft agar. S100P and TMPRSS4 knockdown in PDAC cells significantly reduced anchorage-independent growth compared with the shGFP and control cells in soft agar assays (FIG. 15).

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features herein before set forth.

All publications, patents and patent applications are herein incorporated by reference in their entirety to the same extent as if each individual publication, patent or patent application was specifically and individually indicated to be incorporated by reference in its entirety.

What is claimed is:
1. A method comprising:
   (a) performing an assay to detect an expression level of a panel of genes in a pancreatic tissue sample obtained from a subject, wherein the panel of genes consists of epithelial cell transforming sequence 2 oncogene (ECT2); AHNAK nucleoprotein 2 (AHNAK2); serpin peptidase inhibitor, clade B (ovalbumin) member 5

(SERPINB5); transmembrane protease, serine 4 (TMPRSS4); and periostin, osteoblast specific factor (POSTN); and (b) administering a treatment for pancreatic ductal adenocarcinoma to said subject having increased expression levels of at least three genes of the panel, as compared to a control.

2. The method of claim 1, wherein said expression level is mRNA expression level, cDNA expression level, or protein expression level.

3. The method of claim 1, wherein said sample comprises mRNA, cDNA, and/or protein from said subject.

4. The method of claim 1, further comprising contacting said sample with one or more binding agents capable of specifically binding one or more of said panel of genes or a protein encoded by one or more of said panel of genes.

5. The method of claim 1, further comprising, directly analyzing RNA without extraction and without conversion into cDNA.

6. The method of claim 1, further comprising, prior to determining said expression level, extracting mRNA from said sample and reverse transcribing said mRNA into cDNA to obtain a treated sample.

7. The method of claim 6, further comprising contacting said sample with one or more binding agents capable of specifically binding one or more of said genes or a protein encoded by one or more of said genes.

8. The method of claim 1, wherein said subject is predisposed to developing pancreatic ductal adenocarcinoma.

9. The method of claim 1, wherein said method further comprises determining the level of expression of said panel of genes after administering the treatment, wherein the level of expression of said panel of genes is indicative of the efficacy of the treatment.

10. The method of claim 1, wherein said sample comprises pancreatic juice or bile.

11. The method of claim 1, wherein the control comprises a pancreatic tissue sample from a healthy subject.

12. The method of claim 1, wherein step (a) identifies the subject as having early-stage PDAC, a pre-malignant pancreatic lesion, or PDAC relative to a subject with a normal pancreas, a benign pancreatic lesion, chronic pancreatitis, or a non-pancreatic tumor.

13. The method of claim 1, wherein the subject has early-stage PDAC.

14. The method of claim 13, wherein the early-stage PDAC is pancreatic intraepithelial neoplasia, intraductal papillary-mucinous adenoma, intraductal papillary-mucinous carcinoma, or intraductal papillary-mucinous neoplasm.

15. The method of claim 1, wherein the subject is pre-symptomatic.

16. A method comprising administering a treatment for pancreatic ductal adenocarcinoma to a subject as a result of a determination of an expression level of a panel of genes consisting of ECT2, AHNAK2, SERPINB5, TMPRSS4, and POSTN in a pancreatic tissue sample from the subject, in which the expression level of at least three genes of the panel is increased as compared to a control.

17. The method of claim 16, wherein the control comprises a pancreatic tissue sample from a healthy subject.

\* \* \* \* \*

UNITED STATES PATENT AND TRADEMARK OFFICE
CERTIFICATE OF CORRECTION

PATENT NO. : 10,604,809 B2
APPLICATION NO. : 15/116272
DATED : March 31, 2020
INVENTOR(S) : Roya Khosravifar et al.

It is certified that error appears in the above-identified patent and that said Letters Patent is hereby corrected as shown below:

In the Claims

Column 38, Line 67, replace "glade B" with --clade B--.

Signed and Sealed this
Nineteenth Day of January, 2021

Andrei Iancu
*Director of the United States Patent and Trademark Office*